(12) United States Patent
Gunn et al.

(10) Patent No.: US 8,329,627 B2
(45) Date of Patent: Dec. 11, 2012

(54) LOW-IRRITATING, CLEAR CLEANSING COMPOSITIONS WITH RELATIVELY LOW PH

(75) Inventors: Euen Thomas Graham Ekman Gunn, Hopewell, NJ (US); Russel M. Walters, Philadelphia, PA (US); Lisa R. Gandolfi, Charlotte, NC (US); Kevin C. Lahey, South Plainfield, NJ (US); Mary Catherine Mack, Summit, NJ (US)

(73) Assignee: Johnson & Johnson Consumer Companies, Inc., Skillman, NJ (US)

( * ) Notice: Subject to any disclaimer, the term of this patent is extended or adjusted under 35 U.S.C. 154(b) by 0 days.

(21) Appl. No.: 13/166,445

(22) Filed: Jun. 22, 2011

(65) Prior Publication Data

US 2011/0319308 A1 Dec. 29, 2011

Related U.S. Application Data

(63) Continuation-in-part of application No. 12/976,573, filed on Dec. 22, 2010, and a continuation-in-part of application No. 12/822,329, filed on Jun. 24, 2010.

(51) Int. Cl.
*A61K 8/00* (2006.01)

(52) U.S. Cl. ........ 510/130; 510/426; 510/428; 510/490; 510/505

(58) Field of Classification Search .................. None
See application file for complete search history.

(56) References Cited

U.S. PATENT DOCUMENTS

| | | | |
|---|---|---|---|
| 2,129,264 A | 9/1938 | Downing et al. | |
| 2,178,353 A | 10/1939 | Werntz | |
| 2,774,786 A | 12/1956 | Erickson | |
| 2,813,898 A | 11/1957 | Gaertner | |
| 2,828,332 A | 3/1958 | Gaertner | |
| 3,318,817 A | 5/1967 | Smith | |
| 3,950,260 A | 4/1976 | Eldib | |
| 4,110,263 A | 8/1978 | Lindemann et al. | |
| 4,186,113 A | 1/1980 | Verdicchio et al. | |
| 4,215,064 A | 7/1980 | Lindermann et al. | |
| 4,233,192 A | 11/1980 | Lindermann et al. | |
| 4,372,869 A | 2/1983 | Lindermann et al. | |
| 4,380,637 A | 4/1983 | Lindermann et al. | |
| 4,382,036 A | 5/1983 | Lindermann et al. | |
| 4,443,362 A | 4/1984 | Guth et al. | |
| 4,552,685 A | 11/1985 | Kernstock et al. | |
| 4,617,414 A | 10/1986 | Lukenbach et al. | |
| 4,726,915 A | 2/1988 | Verdicchio | |
| 5,004,557 A | 4/1991 | Nagarajan et al. | |
| 5,130,056 A | 7/1992 | Jakobson et al. | |
| 5,215,976 A | 6/1993 | Fost et al. | |
| 5,286,719 A | 2/1994 | Fost et al. | |
| 5,478,490 A | 12/1995 | Russo et al. | |
| 5,648,348 A | 7/1997 | Fost et al. | |
| 5,650,402 A | 7/1997 | Fost et al. | |
| 6,423,305 B1 | 7/2002 | Cauwet-Martin et al. | |
| 6,468,614 B1 | 10/2002 | LeVine et al. | |
| 6,533,873 B1 | 3/2003 | Margosiak et al. | |
| 6,762,159 B2 | 7/2004 | Ishitobi et al. | |
| 6,897,253 B2 | 5/2005 | Schmucker-Castner et al. | |
| 7,157,414 B2 | 1/2007 | LiBrizzi et al. | |
| 7,335,627 B1 | 2/2008 | O'Lenick et al. | |
| 7,375,064 B1 | 5/2008 | O'Lenick et al. | |
| 7,507,399 B1 | 3/2009 | O'Lenick et al. | |
| 7,547,434 B2 | 6/2009 | Tierney et al. | |
| 7,754,666 B2 | 7/2010 | Walters et al. | |
| 7,803,403 B2 * | 9/2010 | Librizzi et al. ............... 424/487 |
| 2003/0103929 A1 | 6/2003 | Maubru | |
| 2006/0014662 A1 | 1/2006 | Kohut et al. | |
| 2006/0257348 A1 | 11/2006 | Walters et al. | |
| 2007/0111910 A1 * | 5/2007 | Walters et al. ............... 510/130 |
| 2008/0112913 A1 | 5/2008 | Librizzi et al. | |
| 2008/0113895 A1 | 5/2008 | Tamareselvy et al. | |
| 2009/0053337 A1 | 2/2009 | Hansenne et al. | |

FOREIGN PATENT DOCUMENTS

| | | |
|---|---|---|
| DE | 198 18 410 A1 | 10/1999 |
| DE | 10 2008 059445 A1 | 6/2010 |
| EP | 1 010 422 A2 | 6/2000 |
| EP | 1 559 774 A1 | 8/2005 |
| WO | WO 99/21530 A1 | 5/1999 |
| WO | WO 09/016375 A2 | 5/2009 |

OTHER PUBLICATIONS

Rohm and Haas Company (Dow Personal Care) "ACULYN 33 Rheology Modifier/Stablilizer", Brochure (Sep. 2002).
PCT Search Report dated Jan. 11, 2012, for PCT Application No. PCT/US20111/041611.
European Communication dated May 31, 2012 from U.S. Appl. No. 11194698 EP Search Report.

* cited by examiner

*Primary Examiner* — Necholus Ogden, Jr.

(57) ABSTRACT

The methods and compositions of this invention relate to compositions having low irritation characteristics in combination with one or more additional characteristics, for example, relatively high clarity, relatively high foaming, and/or combinations thereof, as well as methods of making and using such compositions. These compositions contain blends of amphoteric surfactants, have low pH values and are useful in cleansing the skin.

4 Claims, No Drawings

LOW-IRRITATING, CLEAR CLEANSING COMPOSITIONS WITH RELATIVELY LOW PH

This application is a continuation-in-part application of U.S. Ser. No. 12/822,329, filed Jun. 24, 2010 and U.S. Ser. No. 12/976,573, filed Dec. 22, 2010, both of which are hereby incorporated herein by reference.

FIELD OF THE INVENTION

The compositions of this invention are useful in cleansing the skin and are characterized by having low irritation characteristics in combination with one or more additional beneficial characteristics, such as, relatively high clarity, relatively high foaming, and/or combinations thereof. The compositions of the present invention generally have low pH values.

BACKGROUND OF THE INVENTION

Synthetic surfactant detergents, such as cationic, anionic, amphoteric, and non-ionic surfactants, are used widely in a variety of detergent and cleansing compositions to impart cleansing properties thereto. In addition these synthetic surfactant detergents have been used in personal care compositions including shampoos and washes. In these personal care compositions, it may be desirable to use combinations and levels of surfactants sufficient to achieve relatively high levels of foam volume and/or foam stability.

However, as is recognized in the art, synthetic surfactant detergents tend to be irritating to the skin and eyes. As concentrations of such detergents increase in personal care compositions so as to impart increased cleansing and foaming properties to these compositions, the irritation associated with such compositions also tends to increase, making them undesirable for use on or near the skin and/or eyes.

Attempts to produce milder cleansing compositions have included combining relatively low amounts of anionic surfactants (which tend to be relatively high-foaming but also relatively highly irritating) with relatively lower irritating surfactants such as nonionic and/or amphoteric surfactants. See, e.g. U.S. Pat. No. 4,726,915. Another approach to producing mild cleansing compositions is to associate the anionic surfactants with amphoteric or cationic compounds in order to yield surfactant complexes. See, e.g., U.S. Pat. Nos. 4,443,362; 4,726,915; 4,186,113; and 4,110,263. Disadvantageously, mild cleansing compositions produced via both of such methods tend to suffer from relatively poor foaming and cleansing performance.

It has further been recognized that, for certain uses, consumers desire cleansing compositions to be relatively clear. In particular, clear compositions are often used advantageously to provide an aesthetic indication of purity to the consumer. However, a number of ingredients commonly used in conventional personal care compositions, including, for example, polymeric thickeners, tend to cause the compositions to become cloudy or opaque. It is not readily predictable which combinations of polymers, surfactants and other optional ingredients may be combined to create compositions that are suitable for use as cleansers and also exhibit high clarity.

Another complicating factor with respect to creating clear compositions is that certain polymeric thickeners require higher pH to maintain clarity and stability in personal care compositions.

U.S. Pat. No. 6,897,253 ('253) describes a substantially crosslinked alkali-swellable acrylate copolymer rheology modifier, water, an alkaline material, and an effective amount of surfactant so that a substantially insoluble compound is stabilized or suspended. The disclosed polymeric rheology modifiers do not start to build substantial viscosity until a pH of about 5 or 6 or higher is achieved. To formulate a composition with a lower pH is difficult but '253 discusses a "Back-Acid" thickening method to achieve clear cleansing systems with an acrylate rheology modifier and high surfactant concentrations (greater than about 9.8% actives) at low pH (about pH 4.5-5). This method involves formulating at a higher pH to obtain the appropriate viscosity and stability and then slowly lowering the pH with an organic acid.

US 2008/0113895 sets forth the use of low molecular weight acrylic polymers with the anionic surfactants sodium laureth sulfate and sodium trideceth sulfate for mild cleansing systems. Clear cleansing system are achieved, but only at pH of greater than 6.5

U.S. Pat. No. 7,803,403 describes the use of low molecular weight acrylic polymers for irritation mitigation and points out the difficulty in creating clear cleansing systems with low molecular weight hydrophobically modified polymers. While clear systems are achieved with low molecular weight acrylic polymer combined with either sodium laureth sulfate, sodium trideceth sulfate, or cocamidopropyl betaine, the pH of the compositions must be 6.5.

It is desirable to formulate skin care compositions, including cleansing compositions, to be as mild as possible to the skin and eyes. One way in which to achieve this goal is by having a composition that has pH that is compatible with the skin and eyes. In addition, there is a need for the compositions to exhibit relatively high clarity, desirable foam properties and/or other desirable aesthetic properties. Additional aspects of skin care compositions involve safety and compatible preservative systems.

The ingredients of the skin care compositions of this invention may also require certain pH parameters. For example, certain active ingredients such salicylic acid, require low pH for activity.

Some preservative systems, preservatives that function in their acidic form and not in there salt form, e.g. sodium benzoate or potassium sorbate, require a low composition pH for efficacy. The efficiency of the preservative decreases with increasing pH, dependent upon the pKa of the preservative. Therefore it is desirable to formulate at low pH to provide maximum efficiency while maintaining a pH compatible with the skin and eyes.

Additionally, it is desirable to formulate compositions to have a pH neutral to the skin, from about 5 to about 6. Cleansers having a pH below that of skin (between about 4 and about 5) may be desired in order to lower the pH of skin for enhanced enzyme function and to alter the skin microflora.

The skin care compositions of this invention have low pH yet have high clarity. The compositions have low irritation characteristics and are clear.

SUMMARY OF THE INVENTION

The compositions of this invention relate to a skin cleansing composition comprising, consisting essentially of and consisting of:

(a) a low molecular weight, non-crosslinked acrylic copolymer in an amount comprising, consisting essentially of and consisting of from about 0.03 weight percent to about 2.1 weight percent of the skin cleansing composition; and (b) a surfactant component comprising, consisting essentially of and consisting of a blend of at least two different amphoteric surfactants selected from the group consisting of: an ampholytic synthetic surfactant comprising a derivative of an aliphatic amine having from 8 to 18 carbon atoms and an anionic water-solubilizing group and zwitterionic surfactants comprising internally neutralized derivatives of aliphatic quaternary ammonium, phosphonium and tertiary sulfonium compounds, in which the aliphatic radical is straight chain or branched and wherein one of the aliphatic substituents has from 8 to 18 carbon atoms and one contains an anionic water-solubilizing group and wherein said surfactant component does not contain cocobetaine, said surfactants being present in a concentration of between about 0.0015 to about 15 weight percent of the skin cleansing composition and the total surfactant load of such composition is less than about 20 weight percent;

(c) wherein the total surfactant load of said skin cleansing composition is not greater than about 14 weight percent of the skin cleansing composition; the pH of said skin cleansing composition is about 6 or less; and the skin cleansing composition has an absorbance of less than about 0.2.

In another aspect of the compositions of this invention, the compositions comprise, consist essentially of and consist of:
(a) water;
(b) a low molecular weight non-crosslinked, linear acrylic copolymer in an amount comprising, consisting essentially of and consisting of from about 0.03 weight percent to about 1.6 weight percent of the skin cleansing composition;
(c) at least two different amphoteric surfactants selected from the group consisting of: an ampholytic synthetic surfactant comprising a derivative of an aliphatic amine having from 8 to 18 carbon atoms and an anionic water-solubilizing group and zwitterionic surfactants comprising internally neutralized derivatives of aliphatic quaternary ammonium, phosphonium and tertiary sulfonium compounds, in which the aliphatic radical is straight chain or branched and wherein one of the aliphatic substituents has from 8 to 18 carbon atoms and one contains an anionic water-solubilizing group; wherein one of such amphoteric surfactants comprises, consists essentially or and consists of coco-betaine in a concentration of less than about 0.065 weight percent or greater than about 3.5 weight percent; said remaining surfactants being present in a concentration of between about 0.0015 to about 15 weight percent of the skin cleansing composition and the total surfactant load of such composition is less than about 20 weight percent;

wherein said skin cleansing composition has a pH of less than about 6 and is substantially free of anionic surfactant, said skin cleansing composition having an absorbance of less than about 0.2.

More preferably, the amphoteric surfactants may be chosen from the group consisting of sodium lauroamphoacetate, cocamidopropyl betaine, cocamidopropyl hydroxysultaine and, where appropriate as set forth above, cocobetaine.

We have found that while systems containing amphoteric surfactants and low molecular weight hydrophilic polymers are clear at pH above about 6.2, they are not generally clear at pH less than about 6. Surprisingly, we have found that surfactants having the structures set forth above and further explicated below tend to improve clarity of detergent compositions containing low molecular weight hydrophilic polymers at pH less than about 6. Such a pH is preferred for formulations that come into contact with the skin in order to be compatible with the skin, as the pH of skin is about 5.5.

DETAILED DESCRIPTION OF THE INVENTION

Applicants have discovered that the skin cleansing compositions of this invention exhibit a unique and unexpected combination of properties including relatively low irritation and relatively high clarity at a lower than expected pH, a pH that is compatible with skin. This makes the compositions of this invention ideal for skin care, including baby and infant skin, cosmetic or cleansing compositions. The compositions include a low molecular weight, non-crosslinked, acrylic copolymer and a surfactant component, which includes at least one non-ethoxylated anionic surfactant and at least one amphoteric surfactant. Surprisingly, using a select group of surfactants to bind with the low molecular weight, non-crosslinked, acrylic copolymer, results in a composition that is clear at a pH lower than previously thought would be possible.

The term "total surfactant load" means the total weight percentage of all surfactants, including both anionic and amphoteric surfactants as well as additional surfactants which may be present in the compositions of this invention. Such additional surfactants may include nonionic surfactants, for example. In accordance with this invention, the total surfactant load of said skin cleansing composition is not greater than about 14 weight percent of the skin cleansing composition As used herein, the term "low pH" shall include pH measurements of less than or equal to about 6.2 as determined by ASTM method E70-07 Standard Test Method for pH of Aqueous Solutions With the Glass Electrode. In a preferred embodiment, the pH range is between about 3.5 and about 6.2. In a more preferred embodiment, the pH range is between about 4 and about 6. In a most preferred embodiment, the pH range is between about 4.5 and about 5. It was previously known that pH also affects certain preservative systems. For example, a high pH reduces the efficacy of preservative system. As detailed below, an organic acid preservative system may become ineffective if the appropriate pH is not maintained.

As used herein, the terminology "relatively high clarity" and/or "clear composition" may be used interchangeably and shall mean that the composition shall have a light transmittance of greater than about 90%, more preferably greater than about 90.5%, and most preferably greater than about 95% as determined by the Clarity Test as defined in the methods section. As used herein, the term "clear composition" shall mean that the composition shall have a count rate of less than about 70 kcts/s, more preferably less than about 50 kcts/s kcts/s, and most preferably less than about 40 kcts/s, as determined by the Light Scattering Test as defined in the methods section.

Amphoteric Synthetic Surfactants

Ampholytic synthetic detergents can be broadly described as derivatives of aliphatic amines which contain a long chain of about 8 to 18 carbon atoms and an anionic water-solubilizing group, e.g., carboxy, sulfo or sulfato. Examples of compounds falling within this definition are sodium 3-dodecylaminopropionate, sodium-3-dodecylamino propane sulfonate, and dodecyl dimethylammonium hexanoate. Other examples of ampholytic and amphoteric surfactants are found in U.S. Pat. No. 3,318,817, issued to Cunningham 15 on May 9, 1967, and hereby incorporated herein by reference.

The specific preferred examples of amphoteric surfactants are those having the formula:

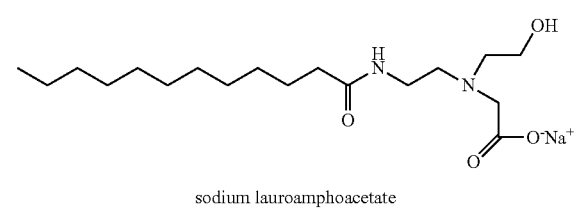

sodium lauroamphoacetate

Zwitterionic Synthetic Surfactants

Zwitterionic surface active agents are broadly described as internally neutralized derivatives of aliphatic quaternary ammonium, phosphonium and tertiary sulfonium compounds, in which the aliphatic radical can be straight chain or branched, and wherein one of the aliphatic substituents contains from about 8 to 18 carbon atoms and one contains an anionic water-solubilizing group, e.g., carboxy, sulfo, sulfato, phosphato, or phosphono. Some of these zwitterionic surfactants are described in the following U.S. Pat. Nos. 2,129,264; 2,178,353; 2,774,786; 2,813,898; and 2,828,332.

The specific preferred examples of zwitterionic surfactants are those having the formula:

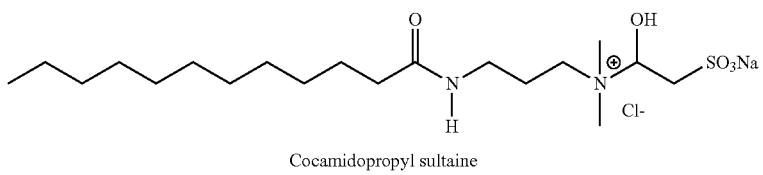

Cocamidopropyl sultaine

The water-soluble betaine surfactants are another example of a zwitterionic surfactant useful herein. These materials have the general formula:

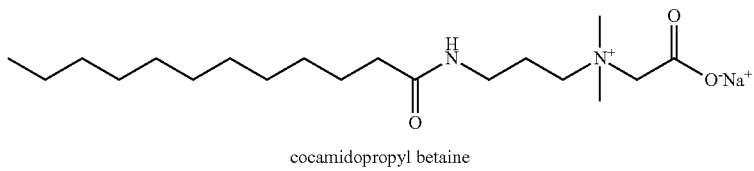

cocamidopropyl betaine

Examples of suitable betaine compounds of this type include dodecyldimethylammonium acetate, tetradecyldimethylammonium acetate, hexadecyldimethylammonium acetate, alkyldimethylammonium acetate wherein the alkyl group averages about 12 to 18 carbon atoms in length, dodecyldimethylammonium butanoate, tetradecyldimethylammonium butanoate, hexadecyldimethylammonium butanoate, dodecyldimethylammonium hexanoate, hexadecyldimethylammonium hexanoate, tetradecyldimethylammonium pentanoate and tetradecyldipropyl ammonium pentanoate. Especially preferred betaine surfactants include dodecyldimethylammonium acetate, dodecyldimethylammonium hexanoate, hexadecyldimethylammonium acetate, and hexadecyldimethylammonium hexanoate.

Polymeric Material

As used herein the term "low molecular weight" polymer refers to a polymer having a number average molecular weight ($M_n$) of about 100,000 or less as measured by gel permeation chromatography (GPC) calibrated with a poly(methyl methacrylate) (PMMA) standard. In certain preferred embodiments, low-molecular weight polymers are those having molecular weight ranges of from about 5,000 to about 80,000 $M_n$, more preferably from about 10,000 to about 50,000 $M_n$, and more preferably between about 15,000 and 40,000 $M_n$.

The polymeric material useful in the composition of this invention is preferably a polymeric material suitable for associating anionic and/or amphoteric surfactant thereto and is preferably a non-crosslinked, linear acrylic copolymer that mitigates the impaired dermal barrier damage typically associated with surfactant systems without substantially increasing viscosity build. The non-crosslinked, linear polymers are preferably of low molecular weight having a number average molecular weight of 100,000 or less as measured by gel permeation chromatography (GPC) calibrated with a poly(methyl methacrylate) (PMMA) standard (as used herein, unless otherwise specified, all number average molecular weights ($M_n$) refer to molecular weight measured in such manner). Thus, the polymeric material functions as a copolymeric mitigant. The copolymeric mitigant is polymerized from at least two monomeric components. The first monomeric component is selected from one or more α,β-ethylenically unsaturated monomers containing at least one carboxylic acid group. This acid group can be derived from monoacids or diacids, anhydrides of dicarboxylic acids, monoesters of diacids, and salts thereof. The second monomeric component is hydrophobically modified (relative to the first monomeric component) and is selected from one or more α,β-ethylenically unsaturated non-acid monomers containing a $C_1$ to $C_9$ alkyl group, including linear and branched $C_1$ to $C_9$ alkyl esters of (meth)acrylic acid, vinyl esters of linear and branched $C_1$ to $C_{10}$ carboxylic acids, and mixtures thereof. In one aspect of the invention the second monomeric component is represented by the formula:

$$CH_2\!=\!CRX$$

wherein R is hydrogen or methyl; X is —C(O)OR$^1$ or —OC(O)R$^2$; R$^1$ is linear or branched $C_1$ to $C_9$ alkyl; and R$^2$ is hydrogen or linear or branched $C_1$ to $C_9$ alkyl. In another aspect of the invention R$^1$ and R$^2$ is linear or branched $C_1$ to $C_8$ alkyl and in a further aspect R$^1$ and R$^2$ are linear or branched $C_2$ to $C_5$ alkyl.

Exemplary first monomeric components include (meth)acrylic acid, itaconic acid, citraconic acid, maleic acid, fumaric acid, crotonic acid, aconitic acid, and mixtures thereof. Exemplary second monomeric components include ethyl(meth)acrylate, butyl (meth)acrylate, 2-ethylhexyl (meth)acrylate, vinyl formate, vinyl acetate, 1-methylvinyl acetate, vinyl propionate, vinyl butyrate, vinyl 2-ethylhexanoate, vinyl pivalate, vinyl neodecanoate, and mixtures thereof. As used herein, the term "(meth)acrylic" acid and "(meth)acrylate" are meant to include the corresponding methyl derivatives of acrylic acid and the corresponding alkyl acrylate For example, "(meth)acrylic" acid refers to acrylic acid and/or methacrylic acid and "(meth)acrylate" refers to alkyl acrylate and/or alkyl methacrylate.

More preferably, said first monomeric component is selected from the group consisting of (meth)acrylic acid and said second monomeric component is selected from the group consisting of at least one C1 to C9 alkyl (meth)acrylate.

The non-crosslinked, linear acrylic copolymer mitigants of the invention can be synthesized via free radical polymerization techniques known in the art. In one aspect of the invention, the amount of the first monomeric component to the second monomeric component utilized ranges from about 20:80 wt. % to about 50:50 wt. %, based on the total weight of all of the monomers in the polymerization medium. In another aspect the weight ratio of the first monomeric component to the second monomeric component is about 35:65 wt. %, and in a further aspect the weight ratio of first monomeric component to second monomeric component is about 25:75 wt. %, all based on the total weight of all monomers in the polymerization medium.

In another aspect emulsion polymerization techniques can be used to synthesize the non-crosslinked, linear acrylic copolymer mitigants of the invention. In a typical emulsion polymerization, a mixture of the disclosed monomers is added with mixing agitation to a solution of emulsifying surfactant, such as, for example, an anionic surfactant (e.g., fatty alcohol sulfates or alkyl sulfonates), in a suitable amount of water, in a suitable reactor, to prepare a monomer emulsion. The emulsion is deoxygenated by any convenient method, such as by sparging with nitrogen, and then a polymerization reaction is initiated by adding a polymerization catalyst (initiator) such as sodium persulfate, or any other suitable addition polymerization catalyst, as is well known in the emulsion polymerization art. The polymerization medium is agitated until the polymerization is complete, typically for a time in the range of about 4 to about 16 hours. The monomer emulsion can be heated to a temperature in the range of about 70 to about 95° C. prior to addition of the initiator, if desired. Unreacted monomer can be eliminated by addition of more catalyst, as is well known in the emulsion polymerization art. The resulting polymer emulsion product can then be discharged from the reactor and packaged for storage or use. Optionally, the pH or other physical and chemical characteristics of the emulsion can be adjusted prior to discharge from the reactor. Typically, the product emulsion has a total solids content in the range of about 10 to about 50 wt. %. Typically, the total polymer content (polymer solids) of the product emulsion is in the range of about 15 to about 45 wt. %, generally not more than about 35 wt. %.

In one aspect, the number average molecular weight ($M_n$) of the linear copolymeric mitigants of this invention as measured by gel permeation chromatography (GPC) calibrated with a poly(methyl methacrylate) (PMMA) standard is 100,000 or less. In another aspect of the invention, the molecular weight ranges between about 5,000 and about 80,000 $M_n$, in a further aspect between about 10,000 and 50,000 $M_n$, and in a still further aspect between about 15,000 and 40,000 $M_n$.

In one aspect of the invention, the linear copolymeric mitigants have a viscosity of 500 mPa·s or less (Brookfield RVT, 20 rpm, spindle no. 1) at a 5 wt. % polymer solids concentration in deionized water and neutralized to pH 7 with an 18 wt. % NaOH solution. The viscosity can range from about 1 to about 500 mPa·s in another aspect, from about 10 to about 250 mPa·s in a further aspect, and from about 15 to about 150 mPa·s in a still further aspect.

Preferably, the low molecular weight, non-crosslinked linear acrylic copolymer is potassium acrylates copolymer.

Any of a variety of non-ethoxylated anionic surfactants may be combined with a polymeric material of this invention to form a cleansing composition according to preferred embodiments of the present invention. Non-ethoxylated anionic surfactants are surfactants that have a negative charge and do not contain any ethoxylated segments, that is to say there are no —(C—C—O)$_v$— segments on the surfactants.

According to certain embodiments, suitable non-ethoxylated anionic surfactants include those selected from the following classes of surfactants: alkyl sulfates, alkyl sulfonates, alkyl monoglyceride sulfonates, alkylaryl sulfonates, alkyl sulfosuccinates, alkyl sulfosuccinamates, alkyl carboxylates, fatty alkyl sulfoacetates, alkyl phosphates, acylglutamates, sarcosinates, taurates, and mixtures of two or more thereof. Examples of certain preferred anionic surfactants include:

alkyl sulfates of the formula

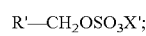
R'—CH$_2$OSO$_3$X';

alkyl monoglyceride sulfates of the formula

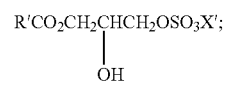
R'CO$_2$CH$_2$CHCH$_2$OSO$_3$X';
|
OH alkyl monoglyceride sulfonates of the formula

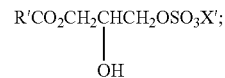
R'CO$_2$CH$_2$CHCH$_2$OSO$_3$X';
|
OH alkyl sulfonates of the formula

R'—SO$_3$X';

alkylaryl sulfonates of the formula

alkyl sulfosuccinates of the formula:

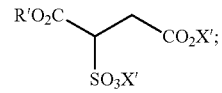

alkyl phosphates
wherein
R' is an alkyl group having from about 7 to about 22, and preferably from about 7 to about 16 carbon atoms,
R'$_1$ is an alkyl group having from about 1 to about 18, and preferably from about 8 to about 14 carbon atoms,
R'$_2$ is a substituent of a natural or synthetic I-amino acid,
X' is selected from the group consisting of alkali metal ions, alkaline earth metal ions, ammonium ions, and ammonium ions substituted with from about 1 to about 3 substituents, each of the substituents may be the same or different and are selected from the group consisting of alkyl groups having from 1 to 4 carbon atoms and hydroxyalkyl groups having from about 2 to about 4 carbon atoms and
w is an integer from 0 to 20;
and mixtures thereof.

According to certain embodiments set forth in U.S. patent application Ser. Nos. 12/822,329 and 12/976,573, the anionic surfactant of this invention is preferably a non-ethoxylated $SO_x$ anionic surfactant conforming to the structure below

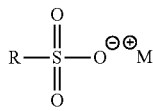

Where $SO_3^-$ is the anionic hydrophilic group, $M^+$ is a monovalent cation (such as $NH_4^+$, $Na^+$, $K^+$, $(HOCH_2CH_2)_3N^+$, etc.), and R comprises any of a broad range of hydrophobic groups and optionally, a) functional groups to link the hydrophilic and hydrophobic moieties and/or b) additional hydrophilic groups. Examples include:

Alkyl sulfonates, where R equals $C_6$-$C_{20}$ alkyl, (linear or branched, saturated or unsaturated), preferably $C_{10}$-$C_{18}$, and most preferably $C_{12}$-$C_{17}$. Specific examples include Sodium C13-C17 Alkane Sulfonate ($R=C_{13}$-$C_{17}$ alkyl, $M^+=Na^+$) and Sodium C14-C17 Alkyl Sec Sulfonate ($R=s$-$C_{13}$-$C_{17}$ alkyl, $M^+=Na^+$)

Alpha olefin sulfonates, where R equals a mixture of

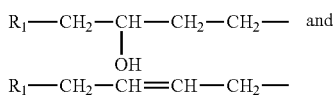

where $R_1=C_4$-$C_{16}$ alkyl or mixtures thereof, preferably $C_6$-$C_{12}$, more preferably $C_8$-$C_{12}$, and most preferably C10-C12. Specific examples include Sodium C12-14 Olefin Sulfonate ($R_1=C_8$-$C_{10}$ alkyl, $M^+=Na^+$) and Sodium C14-16 Olefin Sulfonate ($R_1=C_{10}$-$C_{12}$ alkyl, $M^+=Na^+$).

Alkyl sulfate esters, where $R_1=C_6$-$C_{20}$,

(linear or branched, saturated or unsaturated), preferably C12-C18, more preferably C12-C16, and most preferably C12-C14. Specific examples include Ammonium Lauryl Sulfate ($R_1$=lauryl, $C_{12}H_{25}$, $M^+=NH_4^+$), Sodium Lauryl Sulfate ($R_1$=lauryl, $C_{12}H_{25}$, $M^+=Na^+$), and Sodium Cocosulfate ($R_1$=coco alkyl, $M^+=Na^+$).

As used herein, the term "amphoteric" means: 1) molecules that contain both acidic and basic sites such as, for example, an amino acid containing both amino (basic) and acid (e.g., carboxylic acid, acidic) functional groups; or 2) zwitterionic molecules which possess both positive and negative charges within the same molecule. The charges of the latter may be either dependent on or independent of the pH of the composition. Examples of zwitterionic materials include, but are not limited to, alkyl betaines and amidoalkyl betaines as set forth above and below. The amphoteric surfactants are disclosed herein without a counter ion. One skilled in the art would readily recognize that under the pH conditions of the compositions of this invention, the amphoteric surfactants are either electrically neutral by virtue of having balancing positive and negative charges, or they have counter ions such as alkali metal, alkaline earth, or ammonium counter ions.

Examples of amphoteric surfactants suitable for use in this invention include, but are not limited to, amphocarboxylates such as alkylamphoacetates (mono or di); alkyl betaines; amidoalkyl betaines; alkyl sultaines; amidoalkyl sultaines; amphophosphates; phosphorylated imidazolines such as phosphobetaines and pyrophosphobetaines; carboxyalkyl alkyl polyamines; alkylimino-dipropionates; alkylamphoglycinates (mono or di); alkylamphoproprionates (mono or di),); N-alkyl β-aminoproprionic acids; alkylpolyamino carboxylates; and mixtures thereof.

Examples of suitable amphocarboxylate compounds include those of the formula:

wherein
A is an alkyl or alkenyl group having from about 7 to about 21, e.g. from about 10 to about 16 carbon atoms;
x is an integer of from about 2 to about 6;
$R_5$ is hydrogen or a carboxyalkyl group containing from about 2 to about 3 carbon atoms;
$R_6$ is a hydroxyalkyl group containing from about 2 to about 3 carbon atoms or is a group of the formula:

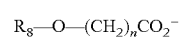

wherein
$R_8$ is an alkylene group having from about 2 to about 3 carbon atoms and n is 1 or 2; and
$R_7$ is a carboxyalkyl group containing from about 2 to about 3 carbon atoms;

Examples of suitable alkyl betaines include those compounds of the formula:

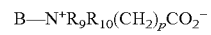

wherein
B is an alkyl or alkenyl group having from about 8 to about 22, e.g., from about 8 to about 16 carbon atoms;
$R_9$ and $R_{10}$ are each independently an alkyl or hydroxyalkyl group having from about 1 to about 4 carbon atoms; and
p is 1 or 2.

A preferred betaine for use in this invention is lauryl betaine, available commercially from Albright & Wilson, Ltd. of West Midlands, United Kingdom as "Empigen BB/J."

Examples of suitable amidoalkyl betaines include those compounds of the formula:

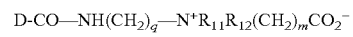

wherein
D is an alkyl or alkenyl group having from about 7 to about 21, e.g. from about 7 to about 15 carbon atoms;
$R_{11}$ and $R_{12}$ are each independently an alkyl or Hydroxyalkyl group having from about 1 to about 4 carbon atoms;
q is an integer from about 2 to about 6; and m is 1 or 2.

One amidoalkyl betaine is cocamidopropyl betaine, available commercially from Goldschmidt Chemical Corporation of Hopewell, Va. under the tradename, "Tegobetaine L7."

Examples of suitable amidoalkyl sultaines include those compounds of the formula

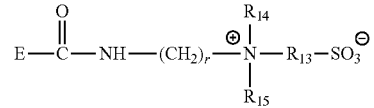

wherein
E is an alkyl or alkenyl group having from about 7 to about 21, e.g. from about 7 to about 15 carbon atoms;
$R_{14}$ and $R_{15}$ are each independently an alkyl, or hydroxyalkyl group having from about 1 to about 4 carbon atoms;
r is an integer from about 2 to about 6; and
$R_{13}$ is an alkylene or hydroxyalkylene group having from
about 2 to about 3 carbon atoms;

In one embodiment, the amidoalkyl sultaine is cocamidopropyl hydroxysultaine, available commercially from Rhone-Poulenc Inc. of Cranbury, N.J. under the tradename, "Mirataine CBS."

Examples of suitable amphophosphate compounds include those of the formula:

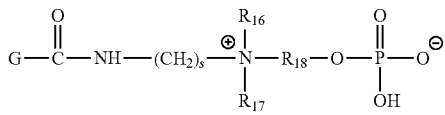

wherein
G is an alkyl or alkenyl group having about 7 to about 21, e.g. from about 7 to about 15 carbon atoms;
s is an integer from about 2 to about 6;
$R_{16}$ is hydrogen or a carboxyalkyl group containing from about 2 to about 3 carbon atoms;
$R_{17}$ is a hydroxyalkyl group containing from about 2 to about 3 carbon atoms or a group of the formula:

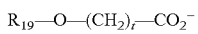

wherein $R_{19}$ is an alkylene or hydroxyalkylene group having from about 2 to about 3 carbon atoms and t is 1 or 2; and
$R_{18}$ is an alkylene or hydroxyalkylene group having from about 2 to about 3 carbon atoms.

In one embodiment, the amphophosphate compounds are sodium lauroampho PG-acetate phosphate, available commercially from Mona Industries of Paterson, N.J. under the tradename, "Monateric 1023," and those disclosed in U.S. Pat. No. 4,380,637, which is incorporated herein by reference.

Examples of suitable phosphobetaines include those compounds of the formula:

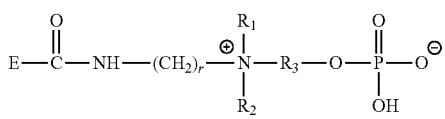

wherein E, r, $R_1$, $R_2$ and $R_3$, are as defined above. In one embodiment, the phosphobetaine compounds are those disclosed in U.S. Pat. Nos. 4,215,064, 4,617,414, and 4,233,192, which are all incorporated herein by reference.

Examples of suitable pyrophosphobetaines include those compounds of the formula:

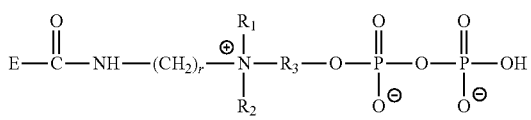

wherein E, r, $R_1$, $R_2$ and $R_3$, are as defined above. In one embodiment, the pyrophosphobetaine compounds are those disclosed in U.S. Pat. Nos. 4,382,036, 4,372,869, and 4,617,414, which are all incorporated herein by reference.

Examples of suitable carboxyalkyl alkylpolyamines include those of the formula:

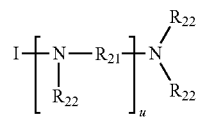

wherein
I is an alkyl or alkenyl group containing from about 8 to about 22, e.g. from about 8 to about 16 carbon atoms;
$R_{22}$ is a carboxyalkyl group having from about 2 to about 3 carbon atoms;
$R_{21}$ is an alkylene group having from about 2 to about 3 carbon atoms and
u is an integer from about 1 to about 4.

Any suitable amounts of polymeric material and surfactants may be used in accord with the compositions and methods of this invention. In certain preferred embodiments, the compositions of this invention comprise, consist essentially of and consist of from greater than zero to about 6 weight percent of polymeric material (based on active amount of polymeric material in the total weight of composition). In certain more preferred embodiments, the compositions comprise, consist essentially of and consist of from about 0.1 to about 4.5 weight percent of polymeric material, more preferably from about 0.1 to about 3.5 weight percent of polymeric material, and even more preferably from about 0.2 to about 2.5 weight percent of polymeric material. In the case of cleansing compositions containing amphoteric blends that are substantially free of anionic surfactants, where the composition does not contain cocobetaine, the polymeric material should be present in an amount between about 0.03 and about 2.1 weight percent of the composition. Where cocobetaine is present as a surfactant, there should be less than about 0.03 weight percent or more than about 1.6 weight percent of polymeric material in the composition.

In certain preferred embodiments, the compositions of this invention comprise, consist essentially of and consist of from about 0.0015 to about 15 weight percent of surfactants based on total active amount of surfactant(s) in the total weight of composition. In certain more preferred embodiments, the compositions comprise, consist essentially of and consist of from about 2 to about 12 weight percent of total surfactants. Preferred embodiment formulas have from about 2 to about 9 weight percent total surfactants. Preferred embodiments have from about 2 to about 7 weight percent total surfactants. In cases in which cocobetaine is present, said cocobetaine should be present in an amount less than about 0.065 weight percent or greater than about 3.5 weight percent in the composition.

When formulating the compositions of the present invention, when the ratio of non-ethoxylated anionic surfactant to amphoteric surfactant is less than 0.5, the pH of the composition should be between 4.8 and about 6. When the ratio of non-ethoxylated anionic surfactant to amphoteric surfactant is greater than 0.5, the pH of the composition can be less than or equal to 6, preferably between 2.5 and 6.

The non-crosslinked, linear acrylic copolymers useful in the compositions of this invention can be synthesized via free radical polymerization techniques known in the art. In one aspect of the invention, the amount of the first monomeric component to the second monomeric component utilized ranges from about 20:80 wt. % to about 50:50 wt. %, based on the total weight of all of the monomers in the polymerization medium. In another aspect the weight ratio of the first monomeric component to the second monomeric component is about 35:65 wt. %, and in a further aspect the weight ratio of first monomeric component to second monomeric component is about 25:75 wt. %, all based on the total weight of all monomers in the polymerization medium.

The cleansing compositions produced, as well as any of the compositions containing polymeric material and a surfactant component having at least one non-ethoxylated anionic surfactant and at least one amphoteric surfactant that are combined in the combining step according to the methods of this invention may further contain any of a variety of other components nonexclusively including additives which enhance the appearance, feel and fragrance of the compositions, such as colorants, fragrances, preservatives, pH adjusting agents and the like.

Any of a variety of nonionic surfactants are suitable for use in the compositions of this invention, keeping in mind that total surfactant load should not exceed about 14 weight percent of the compositions set forth herein. Examples of suitable nonionic surfactants include, but are not limited to, fatty alcohol acid or amide ethoxylates, monoglyceride ethoxylates, sorbitan ester ethoxylates, alkyl polyglucosides, polyglyceryl esters, mixtures thereof, and the like. Certain preferred nonionic surfactants include alkyl polyglucosides, such as but not limited to coco-glucoside and decyl-glucoside, and polyglyceryl esters, such as but not limited to polyglyceryl-10 laurate and polyglyceryl-10 oleate.

Any of a variety of commercially available secondary conditioners, such as volatile silicones, which impart additional attributes, such as gloss to the hair are suitable for use in this invention. In one embodiment, the volatile silicone conditioning agent has an atmospheric pressure boiling point less than about 220° C. The volatile silicone conditioner may be present in an amount of from about 0 percent to about 3 percent, e.g. from about 0.25 percent to about 2.5 percent or from about 0.5 percent to about 1 percent, based on the overall weight of the composition. Examples of suitable volatile silicones nonexclusively include polydimethylsiloxane, polydimethylcyclosiloxane, hexamethyldisiloxane, cyclomethicone fluids such as polydimethylcyclosiloxane available commercially from Dow Corning Corporation of Midland, Mich. under the tradename, "DC-345" and mixtures thereof, and preferably include cyclomethicone fluids.

Any of a variety of commercially available humectants, which are capable of providing moisturization and conditioning properties to the personal cleansing composition, are suitable for use in this invention. The humectant may be present in an amount of from about 0 percent to about 10 percent, e.g. from about 0.5 percent to about 5 percent or from about 0.5 percent to about 3 percent, based on the overall weight of the composition. Examples of suitable humectants nonexclusively include 1) water soluble liquid polyols selected from the group comprising glycerine, propylene glycol, hexylene glycol, butylene glycol, dipropylene glycol, and mixtures thereof; 2) polyalkylene glycol of the formula: HO—(R"O)$_b$—H, wherein R" is an alkylene group having from about 2 to about 3 carbon atoms and b is an integer of from about 2 to about 10; 3) polyethylene glycol ether of methyl glucose of formula $CH_3$—$C_6H_{10}O_5$—$(OCH_2CH_2)_c$—OH, wherein c is an integer from about 5 to about 25; 4) urea; and 5) mixtures thereof, with glycerine being the preferred humectant.

Examples of suitable chelating agents include those which are capable of protecting and preserving the compositions of this invention. Preferably, the chelating agent is ethylenediamine tetracetic acid ("EDTA"), and more preferably is tetrasodium EDTA, available commercially from Dow Chemical Company of Midland, Mich. under the tradename, "Versene 100XL" and is present in an amount, based upon the total weight of the composition, from about 0 to about 0.5 percent or from about 0.05 percent to about 0.25 percent.

Suitable preservatives include organic acid preservatives may include benzoic acid and alkali metal and ammonium salts thereof (e.g. sodium benzoate), sorbic acid and alkali metal and ammonium salts thereof (e.g. potassium sorbate), p-Anisic acid and alkali metal and ammonium salts thereof, and salicylic acid and alkali metal and ammonium salts thereof. The pH of the composition may be adjusted to the appropriate acidic value using any cosmetically acceptable organic or inorganic acid, such as citric acid, acetic acid, glycolic acid, lactic acid, malic acid, tartaric acid, or hydrochloric acid.

In one embodiment of the composition, sodium benzoate is present in the composition in an amount, based upon the total weight of the composition, from about 0 to about 0.5 percent. In another embodiment, potassium sorbate is present in the composition in an amount, based upon the total weight of the composition, from about 0 to about 0.6 percent, more preferably from about 0.3 to about 0.5 percent.

The methods of this invention may further comprise, consist essentially of and consist of any of a variety of steps for mixing or introducing one or more of the optional components described hereinabove with or into a composition comprising a polymeric material before, after, or simultaneously with the combining step described above. While in certain embodiments, the order of mixing is not critical, it is preferable, in other embodiments, to pre-blend certain components, such as the fragrance and the nonionic surfactant before adding such components into a composition comprising a polymeric material and/or an anionic surfactant.

The cleansing methods of this invention may further include any of a variety of additional, optional steps associated conventionally with cleansing hair and skin including, for example, lathering, rinsing steps, and the like.

Although applicants do not wish to be bound by or to any particular theory of operation, it is believed that surfactant associated with the low molecular weight hydrophobically-modified polymer (hm-polymer) is more stable than surfactants that exist as a micelle. Thus, surfactant contained in a micelle structure more readily disperses out of the micelle than it does when associated with low molecular weight hydrophobically-modified polymer.

The foregoing information regarding low molecular weight hydrophobically-modified polymers as well as compositions that may be useful in the methods of this invention are set forth in U.S. Pat. No. 7,803,403, US2006/0257348, and US20070111910, all of which are hereby incorporated herein by reference.

The methods and compositions of this invention illustratively disclosed herein suitably may be practiced in the absence of any component, ingredient, or step which is not specifically disclosed herein. Several examples are set forth below to further illustrate the nature of the invention and the manner of carrying it out. However, the invention should not be considered as being limited to the details thereof.

Methods

Clarity Test:

The clarity of each sample was measured via the Clarity Test, the procedure for which involves preparing a 1 cm cell sample of the composition to be measured and measuring the % light transmittance associated with such sample using an Agilent 8453 UV-Visible Spectrophotometer with a 1 cm cell at a wavelength of 800 nm. The clarity was determined for each cleansing composition without dilution. The results are reported as % T, the % transmittance through cleansing composition in the 1 cm cell.

Light Scattering Test:

The clarity of a cleanser is determined by colloidal assembles that scatter light. A cleanser that is clearer typically will have only small colloidal assemblies. Larger colloidal assemblies, on the order of ⅓ the wavelength of light, will scatter light and produce a hazy or turbid solution.

The cleanser samples were analyzed using a Zetasizer Nano ZS DLS instrument (Malvern Instruments, Inc., Southborough, Mass.) operating at 25.0° C. The instrument was integrated with the Malvern Dispersion Technology Software. The unfiltered sample solutions was diluted to 3% and dispensed into cuvettes (12 mm Square Polystyrene Cuvettes, DTS0012) to the 10 mm mark, and covered. The measurements were done at attenuation 7, with a 4 mW He—Ne, 633 nm laser at position 4.65 mm. The temperature was kept constant at 25 degrees Celsius. Measurements were done in 3 repetitions and 11 runs each.

The laser (at 633 nm) is incident on the cleansing composition and scatters from colloidal assemblies back to the detector. A hazy cleansing solution will have more and larger colloidal particles therefore producing more scattering to the detector and a higher count rate.

Cleansing Formulation Mixing Procedure

Solutions were created in 96-well plates using a serial dilution method with a Hamilton Microlab Starlet high throughput liquid handler. Each plate comprised of one or two amphoteric surfactants and/or low molecular weight hydrophilic polymer. Four different surfactant ratios were run on the same plate producing 24 different solutions for each ingredient combination and a specific Potassium Acrylates Copolymer aqueous solution was used as the diluting agent.

Materials:

A low molecular weight hydrophobically modified polymer, Potassium Acrylates Copolymer (Lubrizol, Brecksville, Ohio) was used in the compositions of this invention as the low molecular weight hydrophobically modified polymer.

The amphoteric surfactants used were: Sodium Lauroamphoacetate (SLAC) sold under the trade-name Miranol Ultra L-32, (Rhodia, Cranbury, N.J.), Cocamidopropyl Hydroxysultaine (CPHS) sold under the trade-name Mackam CBS-50G, (Rhodia, Cranbury, N.J.), Cocamidopropyl Betaine (CAPB) sold under the trade-name Tego Betain L 7V, (Evonik, Hopewell, Va.), and Coco-betaine (CB) sold under the trade-name Dehyton AB-30, (Cognis, Cincinnati, Ohio) Stock solutions were created which consisted of 15% by weight of amphoteric surfactants and a series of solutions with different concentrations of Potassium Acrylates Copolymer. The pH of each of these stock solutions of surfactant and water or polymer and water was measured and adjusted to the desired pH. Surfactant solutions and water were added to the initial well, then this solution was 21 times with the Potassium Acrylates Copolymer solution in sequential fashion to produce dilutions of 75%, 50%, 37.5%, 25%, 18.75%, 12.5%, 9.375%, 6.25%, 4.6875%, 3.125%, 2.34375%, 1.5625%, 1.171875%, 0.78125%, 0.585938%, 0.390625%, 0.292969%, 0.195313%, 0.146484%, 0.097656%, and 0.073242%. After the serial dilution, each well contained a total volume of 80 μl except for column 11 on the well plate, which contained 160 μl. For this column, absorbance was adjusted to reflect the increased amount of material in these wells. Column 12 on the well plate was reserved for a diluting agent control and did not incorporate any amphoteric surfactant.

Clarity Absorbance Test

Upon completion of the serial dilution in the liquid handler, the well plate with the 96 different solutions was transferred to the Molecular Devices Spectra Max 340 PC spectrophotometer and any bubbles removed to avoid possibly interfering with the measurements. Then the absorbance at a wavelength of 410 nm was measured for each solution within 5 minutes of completion of each plate.

The following examples exemplify, but do not limit, the compositions of this invention.

Example 1

Comparatives C1-C4

Preparation of Cleansing Compositions

The cleansing compositions of C1-C4 were prepared according to the materials and amounts listed in Table

TABLE 1

| Trade Name | INCI name | C1 w/w % | C2 w/w % | C3 w/w % | C4 w/w % |
|---|---|---|---|---|---|
| Cedepal TD-403 (30%) | Sodium Trideceth Sulfate | 2.70 | 2.70 | 2.70 | 2.70 |
| Tegobetaine L-7V (30%) | Cocamidopropyl Betaine | 2.70 | 2.70 | 2.70 | 2.70 |
| Merquat S | Polyquaternium-7 | 0.01 | 0.01 | 0.01 | 0.01 |
| Versene 100 XL | Tetrasodium EDTA | 0.10 | 0.10 | 0.10 | 0.10 |
| Aqua SF-1 (30%) | Acrylates Copolymer | — | 1.80 | — | — |
| Ex-968 (30%) | Potassium Acrylates Copolymer | — | — | 1.80 | — |
| Inutec SP-1 | Inulin Lauryl Carbamate | — | — | — | 1.80 |
| 20% NaOH | Sodium Hydroxide | qs | qs | qs | qs |
| Deionized water | Water | qs | qs | qs | qs |

*expressed in % w/w actives

Each of the compositions of Table 1 was independently prepared as follows: Water (50.0 parts) was added to a beaker. The following ingredients were then added thereto independently with mixing until each respective resulting mixture was homogenous: the hm-polymer (Ex. 968, Aqua SF-1, Inutec SP-1, etc. depending on the example), Cedepal TD403MF-D, Tegobetaine L7-V, Merquat S, Versene 100XL, and Nipasept. The pH of the resulting solution was then adjusted with a 20% solution of Citric Acid or Sodium hydroxide solution until the final desired pH was obtained. The remainder of the water was then added thereto. Formulas with the same components, but different pH's were all made independently.

Example 2

Clarity Results for Samples C1-C4 at Different pH's

The clarity of compositions of C1-C4 determined according to the Clarity test.

TABLE 2

| Ex | Base | hydrophobically-modified Polymer added | pH | Clarity (% T) |
|---|---|---|---|---|
| C1 | — | No polymer | 6.3-6.6 | 99.1 |
| C2 | — | Acrylates copolymer | 6.3-6.6 | 88.3 |
| C3 | — | Potassium Acrylates Copolymer | 6.3-6.6 | 98.8 |
| C4 | — | Inulin Lauryl Carbamate | 6.3-6.6 | 37.1 |
| C2 | — | Acrylates copolymer | 4.0 | 18.0 |
| C3 | — | Potassium Acrylates Copolymer | 4.0 | 24.1 |
| C4 | — | Inulin Lauryl Carbamate | 4.0 | 36.4 |

TABLE 2-continued

| Ex | Base | hydrophobically-modified Polymer added | pH | Clarity (% T) |
|---|---|---|---|---|
| | JBS | Potassium Acrylates Copolymer | 6.5 | 95.3 |
| | JBS | Potassium Acrylates Copolymer | 4.8 | 27.5 |
| | HTT | Potassium Acrylates Copolymer | 6.5 | 93.9 |
| | HTT | Potassium Acrylates Copolymer | 4.8 | 17.7 |

Table 2 shows the results of the clarity test of a series of cleansing compositions (C1-C4) containing a series of low molecular weight hydrophobically-modified polymers and a combination of ethoxylated anionic surfactant and amphoteric surfactant, Sodium Trideceth Sulfate and Cocamidopropyl Betaine, respectively as described in Table 1. While the clarity of the cleansing compositions are clear (i.e. have a % Transmittance as measured by the Clarity test greater than about 90%) at high pH, around about 6.3, the clarity is much lower at lower pH. Six grams of the low molecular weight hydrophobically-modified polymer potassium acrylates copolymer were added to 94 grams samples of each of the commercial products JBS (Johnson's Baby Shampoo which contains the ingredients as listed on the label (Water, Cocamidopropyl Betaine, PEG-80 Sorbitan Laurate, Sodium Trideceth Sulfate, PEG-150 Distearate, Fragrance, Tetrasodium EDTA, Polyquaternium-10, Quaternium-15, Sodium Hydroxide, Citric Acid, D&C Yellow 10, D&C Orange 4) and HTT (Johnson's Head-to-Toe Body Baby Wash which contains the ingredients as listed on the label (Water, Cocamidopropyl Betaine, PEG-80 Sorbitan Laurate, Sodium Laureth Sulfate, PEG-150 Distearate, Tetrasodium EDTA, Sodium Chloride, Polyquaternium-10, Fragrance, Quaternium-15, Citric Acid). The new clarity of the new compositions was measured by the Clarity test. The clarity of the cleansing compositions is greater than about 90% (clear) at high pH, around about 6.3, and the clarity is lower at lower pH. In U.S. Pat. No. 7,803,403 cleansing systems containing sodium trideceth sulfate or sodium laureth sulfate and commercial products JBS and HTT were evaluated. While U.S. Pat. No. 7,803,403 shows clear cleansing systems with a low molecular weight linear acrylic polymer and these surfactants, when these systems are prepared at lower pH (below about a pH of 6.2) the cleansing systems lose clarity and become hazy and translucent.

Example 3

Comparatives C5-C11

Preparation of Cleansing Compositions

The cleansing compositions of C5-C11 were prepared according to the materials and amounts listed in Table 3.

TABLE 3

| INCI name | C5 w/w % | C6 w/w % | C7 w/w % | C8 w/w % | C9 w/w % | C10 w/w % | C11 w/w % |
|---|---|---|---|---|---|---|---|
| Sodium Benzoate | 0.50 | 0.50 | 0.50 | 0.50 | 0.50 | 0.50 | 0.50 |
| Potassium Acrylates Copolymer | 1.80 | 1.80 | 1.80 | 1.80 | 1.80 | 1.80 | 1.80 |
| Cocamidopropyl hydroxysultaine | — | 3.40 | — | — | — | — | — |
| Decyl Glucoside | — | — | 3.70 | — | — | — | — |
| Cocamidopropyl betaine | — | — | — | 2.1 | 4.4 | — | — |
| Disodium lauroamphodiacetate | — | — | — | — | — | 2.5 | 5.3 |
| Sodium hydroxide | q.s. | q.s. | q.s. | q.s. | q.s. | q.s. | q.s. |
| Water | q.s. | q.s. | q.s. | q.s. | q.s. | q.s. | q.s. |

*expressed in w/w % actives

Each of the compositions of Table 3 was independently prepared as follows: Water (50.0 parts) was added to a beaker. The following ingredients were then added thereto independently with mixing until each respective resulting mixture was homogenous: the hydrophobically-modified polymer Potassium Acrylates Copolymer (Ex. 968, Lubrizol, Brecksville, Ohio), then the surfactant Cocamidopropyl hydroxysultaine, Decyl Glucoside, Cocamidopropyl betaine, or Disodium lauroamphodiacetate as called for. The pH of the resulting solution was then adjusted with a 20% solution of Sodium hydroxide or citric acid until the final desired pH was obtained. The remainder of the water was then added thereto. Formulas with the same components, but different pH's were all made independently.

Example 4

Clarity Results for samples C5-C11 at Different pH's

The clarity of compositions of C5-C11 determined according to the Clarity test.

TABLE 4

| Ex | Surfactant Type | Surfactant | Surfactant (w/w %) | pH | Clarity (% T) |
|---|---|---|---|---|---|
| C5 | — | No surfactant: hydrophobically-modified polymer at 1.8% | 0 | 4.0 | 3.8 |
| C6 | Amphoteric | Cocamidopropyl hydroxysultaine | 3.4 | 5.0 | 86.9 |
| C6 | Amphoteric | Cocamidopropyl hydroxysultaine | 3.4 | 6.0 | 84.2 |
| C7 | Non-ionic | Decyl Glucoside | 3.7 | 5.0 | 86.7 |
| C7 | Non-ionic | Decyl Glucoside | 3.7 | 6.0 | 83.4 |
| C8 | Amphoteric | Cocamidopropyl betaine | 2.1 | 4.0 | Separated |
| C9 | Amphoteric | Cocamidopropyl betaine | 4.4 | 4.0 | Separated |
| C10 | Amphoteric | Disodium lauroamphoacetate | 2.5 | 4.0 | Separated |
| C11 | Amphoteric | Disodium lauroamphoacetate | 5.3 | 4.0 | Separated |

As shown in Table 4, the low molecular weight (hereinafter, "Mw") hydrophobically-modified polymer without surfactant, C5, at a low pH of 4.0 has a low clarity. As shown in Table 2, clear cleansing compositions are readily made at moderate pH's (pH between about 6.3-6.6) with the low molecular weight linear acrylic polymer, Potassium Acrylates Copolymer, and a number of different types of surfactant systems. Table 4 shows cleansing compositions that are not clear (% T less than about 90%) at low pH: the low molecular weight linear acrylic polymer, Potassium Acrylates Copolymer, and the amphoteric and non-ionic surfactants, Cocamidopropyl hydroxysultaine and Decyl Glucoside respectively. Table 4 also shows cleansing compositions that phase separate and form a white precipitate at low pH, Cocamidopropyl betaine and Disodium lauroamphodiacetate, respectively. This phase separation was present at low and high surfactant concentrations.

Example 5

Comparatives C12-C18

Preparation of Cleansing Compositions

The cleansing compositions of C12-C18 were prepared according to the materials and amounts listed in Table 5.

TABLE 5

| INCI name | C12 w/w % | C13 w/w % | C14 w/w % | C15 w/w % | C16 w/w % | C17 w/w % | C18 ww % |
|---|---|---|---|---|---|---|---|
| Sodium Benzoate | 0.50 | 0.50 | 0.50 | 0.5 | 0.5 | 0.50 | 0.50 |
| Potassium Acrylates Copolymer | 1.80 | 1.80 | 1.80 | 1.8 | 1.80 | 1.80 | 1.80 |
| Sodium Trideceth Sulfate | 2.70 | — | — | — | — | — | — |
| Sodium Laureth Sulfate | — | 0.80 | 4.60 | — | — | — | — |
| Sodium Alpha Olefin Sulfonate | — | — | — | 2.00 | 3.90 | — | — |
| Sodium Coco Sulfate | — | — | — | — | — | 1.80 | 3.70 |
| Sodium hydroxide | q.s. | q.s. | q.s. | q.s. | q.s. | q.s. | q.s. |
| Water | q.s. | q.s. | q.s. | q.s. | q.s. | q.s. | q.s. |

*expressed in w/w % actives

Each of the compositions of Table 5 was independently prepared as follows: Water (50.0 parts) was added to a beaker. The following ingredients were then added thereto independently with mixing until each respective resulting mixture was homogenous: the hydrophobically-modified polymer, Potassium Acrylates Copolymer (Ex. 968, Lubrizol, Brecksville, Ohio), then the surfactant Sodium Trideceth Sulfate, Sodium Laureth Sulfate, Sodium Alpha Olefin Sulfonate, or Sodium Coco Sulfate was added as called for. The pH of the resulting solution was then adjusted with a 20% solution Sodium hydroxide or Citric acid until the final desired pH was obtained. The remainder of the water was then added thereto. Formulas with the same components, but different pH's were all made independently.

Example 6

Clarity Results for Samples C12-C18 at Different pH's

The clarity of compositions of C12-C18 was determined according to the Clarity test.

TABLE 6

| Ex | Surfactant Type | Surfactant | Surfactant (w/w %) | pH | Clarity (% T) |
|---|---|---|---|---|---|
| C12 | Ethoxylated | Sodium Trideceth Sulfate | 2.7 | 4.0 | 81.9 |
| C13 | Ethoxylated | Sodium Laureth Sulfate | 0.8 | 4.0 | 78.8 |
| C14 | Ethoxylated | Sodium Laureth Sulfate | 4.6 | 4.0 | 88.7 |
| C15 | Anionic non-EO | Sodium Alpha Olefin Sulfonate | 2.0 | 4.0 | 86.1 |
| C16 | Anionic non-EO | Sodium Alpha Olefin Sulfonate | 3.9 | 4.0 | 95.7 |

TABLE 6-continued

| Ex | Surfactant Type | Surfactant | Surfactant (w/w %) | pH | Clarity (% T) |
|---|---|---|---|---|---|
| C17 | Anionic non-EO | Sodium Coco Sulfate | 1.8 | 4.0 | 83.7 |
| C18 | Anionic non-EO | Sodium Coco Sulfate | 3.7 | 4.0 | 99.6 |

As shown in Table 2, clear cleansing compositions are readily made at moderate pH's (pH between about 6.3 and about 6.6) with the low molecular weight linear acrylic polymer, Potassium Acrylates Copolymer, and a number of different types of surfactant systems. However in Table 2, when these cleansing compositions are taken to low pH (below a pH of about 6.2), they lose clarity. Furthermore, the lower pH cleansing compositions C12-C14 contain a range of ethoxylated anionic surfactants over a range of levels, none of which achieve clear systems at low pH.

Cleansing compositions with the low molecular weight linear acrylic polymer, Potassium Acrylates Copolymer, and a low amount of non-ethoxylated anionic surfactant, Sodium Alpha Olefin Sulfonate and Sodium Coco Sulfate, C15 and C17, respectively, also have low clarity. However, cleansing systems with the low molecular weight linear acrylic polymer, Potassium Acrylates Copolymer, and non-ethoxylated anionic surfactant can achieve high clarity, C16 and C18. A sufficient amount of anionic surfactant, more than about 2.0% actives, is requirement to achieve a sufficiently clear formula.

Example 7

Comparative Examples C19-25

Non-Ethoxylated Anionic Surfactant Cleansing Compositions and Clarity

The cleansing compositions of C19-25 were prepared according to the materials and amounts listed in Table 7.

TABLE 7

| INCI name | C19 w/w % | C20 w/w % | C21 w/w % | C22 w/w % | C23 w/w % | C24 w/w % | C25 w/w % |
|---|---|---|---|---|---|---|---|
| Sodium Benzoate | 0.5 | 0.5 | 0.5 | 0.50 | 0.50 | 0.50 | 0.5 |
| Potassium Acrylates Copolymer | 1.80 | 1.80 | 1.80 | 1.80 | 1.80 | 1.80 | 1.80 |
| Ammonium Lauryl Sulfate | 3.4 | — | — | — | — | — | — |
| Sodium Dodecyl Benzene Sulfonate | — | 8.40 | 16.8 | — | — | — | — |
| Sodium Lauryl Sulfate | — | — | — | 12.0 | — | — | — |
| Sodium Tridecyl Sulfate 303 | — | — | — | — | 3.4 | — | — |
| Sodium Tridecyl Sulfate 203 | — | — | — | — | — | 3.4 | — |
| Sodium Tridecyl Sulfate Agt | — | — | — | — | — | — | 3.4 |
| Sodium Hydroxide | q.s. | q.s. | q.s. | q.s. | q.s. | q.s. | q.s. |
| Water | q.s. | q.s. | q.s. | q.s. | q.s. | q.s. | q.s. |

*expressed in % w/w actives

Each of the compositions of Table 7 was independently prepared as follows: Water (50.0 parts) was added to a beaker. The following ingredients were then added thereto independently with mixing until each respective resulting mixture was homogenous: the hydrophobically-modified polymer, Potassium Acrylates Copolymer (Ex. 968, Lubrizol, Brecksville, Ohio), then the surfactant Ammonium Lauryl Sulfate, Sodium Dodecyl Benzene Sulfonate, Sodium Lauryl Sulfate, or Sodium Tridecyl Sulfate as called for. The pH of the resulting solution was then adjusted with a 20% solution Sodium hydroxide or Citric acid until the final desired pH was obtained. The remainder of the water was then added thereto. Formulas with the same components, but different pH's were all made independently.

Example 8

Clarity Results for Comparative Examples C16, 18-25 at Different pH's

The clarity of compositions of C16, 18-25 was determined according to the Clarity test.

TABLE 8

| Ex | Surfactant Type | Surfactant | Surfactant (w/w %) | pH | Clarity (% T) | Count rate (@7) kcts/s |
|---|---|---|---|---|---|---|
| C16 | Anionic non-EO | Sodium Alpha Olefin Sulfonate | 3.9 | 4.0 | 95.7 | — |
| C16 | Anionic non-EO | Sodium Alpha Olefin Sulfonate | 3.9 | 5.0 | 99.4 | — |
| C16 | Anionic non-EO | Sodium Alpha Olefin Sulfonate | 3.9 | 6.5 | 99.4 | — |
| C18 | Anionic non-EO | Sodium Coco Sulfate | 3.7 | 4.0 | 99.6 | — |
| C18 | Anionic non-EO | Sodium Coco Sulfate | 3.7 | 5.0 | 99.9 | — |
| C18 | Anionic non-EO | Sodium Coco Sulfate | 3.7 | 6.5 | 99.6 | — |
| C19 | Anionic non-EO | Ammonium Lauryl Sulfate | 3.4 | 4.0 | 100.0 | 36.7 |
| C19 | Anionic non-EO | Ammonium Lauryl Sulfate | 3.4 | 5.0 | 100.0 | — |
| C19 | Anionic non-EO | Ammonium Lauryl Sulfate | 3.4 | 6.5 | 100.0 | — |
| C20 | Anionic non-EO | Sodium dodecyl benzene sulfonate | 8.4 | 4.0 | 90.6 | — |
| C21 | Anionic non-EO | Sodium dodecyl benzene sulfonate | 16.8 | 4.0 | 98.2 | 18.8 |
| C21 | Anionic non-EO | Sodium dodecyl benzene sulfonate | 16.8 | 5.0 | 99.7 | — |
| C22 | Anionic non-EO | Sodium Lauryl Sulfate | 12.0 | 5.0 | 99.8 | 10.1 |
| C22 | Anionic non-EO | Sodium Lauryl Sulfate | 12.0 | 6.5 | 97.9 | — |
| C23 | Anionic non-EO | Sodium Tridecyl Sulfate 303 | 3.4 | 4.5 | 98.9 | — |
| C23 | Anionic non-EO | Sodium Tridecyl Sulfate 303 | 3.4 | 6.5 | 100 | — |
| C24 | Anionic non-EO | Sodium Tridecyl Sulfate 203 | 3.4 | 4.5 | 99.4 | — |
| C24 | Anionic non-EO | Sodium Tridecyl Sulfate 203 | 3.4 | 6.5 | 99.9 | — |
| C25 | Anionic non-EO | Sodium Tridecyl Sulfate Agt | 3.4 | 4.5 | 97.4 | — |
| C25 | Anionic non-EO | Sodium Tridecyl Sulfate Agt | 3.4 | 6.5 | 98.3 | — |

All of the cleansing compositions in Table 8, C16, 18-25, contain the low Mw hydrophobically-modified polymer, Potassium Acrylates copolymer, and a range of non-ethoxylated anionic surfactants at levels above 2.0% actives, and all of these cleansing compositions have high clarity as measured by the Clarity test and or the Light Scattering test (clarity when the count rate is less than about 70 kcts/s). In cleansing compositions with low MW hydrophobically-modified polymer and non-ethoxylated anionic surfactants, at levels between about 9.0 wt % actives and about 2.0 wt % actives, the clarity of the compositions was high even at low pH.

Example 9

Comparative Examples C26-C31

Non-ethoxylated Anionic Surfactant—Amphoteric Surfactant Cleansing Compositions

The cleansing compositions of C26-C31 were prepared according to the materials and amounts listed in Table 9.

TABLE 9

| INCI Name | C26 w/w % | C27 w/w % | C28 w/w % | C29 w/w % | C30 w/w % | C31 w/w % |
|---|---|---|---|---|---|---|
| Glycerin | 0.50 | 0.50 | 0.50 | 0.50 | 0.50 | 0.50 |
| Sodium Coco-Sulfate | 1.66 | | | | | |
| Sodium Lauryl Sulfoacetate | 1.30 | | | | | |
| Sodium Lauryl Sulfosuccinate | | | | 3.00 | | |
| Sodium C14-16 Olefin Sulfonate | | | | | | 2.82 |
| Ammonium Lauryl Sulfate | | 1.82 | 0.91 | | | |
| Sodium Isotridecyl Alcohol Sulfate | | | | 2.78 | 1.26 | |
| Cocamidopropyl Betaine | 6.30 | 4.38 | 2.19 | 4.38 | 2.92 | 0.70 |
| Cocamidopropyl Hydroxysultaine | 3.36 | | | | | |
| Polyglyceryl-10 Laurate | 1.00 | | | | | |
| hydrophobically-modified polymer Potassium Acrylates Copolymer | 0.30 | 0.30 | 0.30 | 0.60 | 0.30 | 0.90 |
| Polyquaternium-7 | 0.08 | | | | | |
| Sodium Benzoate | | | | | 0.50 | 0.50 |
| Potassium Sorbate | | 0.50 | 0.50 | | | |
| Dowicil 200 | | | | 0.05 | | |
| Phenoxyethanol; Ethylhexylglycerin (Euxyl PE9010) | 0.80 | | | | | |
| Fragrance | 0.20 | 0.20 | 0.20 | 0.20 | 0.20 | 0.20 |
| Sodium Hydroxide | QS | QS | QS | QS | QS | QS |
| Citric Acid | QS | QS | QS | QS | QS | QS |
| Water | QS | QS | QS | QS | QS | QS |

*expressed in % w/w actives

Each of the compositions of Table 9 was prepared as follows: Water (50.0 parts) was added to a beaker. The following ingredients were then added thereto independently with mixing and/or heating until each respective resulting mixture was homogenous: Polyglyceryl-10 Laurate and Sodium Lauryl Sulfoacetate with heat to 70° C. Then the heat was removed and the mixture was allowed to cool while the following ingredients were added: glycerin, then the surfactants, Sodium Lauryl Sulfosuccinate, Sodium C14-16 Olefin Sulfonate, Ammonium Lauryl Sulfate, Sodium Isotridecyl Alcohol Sulfate, Sodium Coco-Sulfate, Cocamidopropyl Betaine, and/or Cocamidopropyl Hydroxysultaine, and then Polyquaternium-7 where required, then the hydrophobically-modified polymer, Potassium Acrylates Copolymer (Ex. 968, Lubrizol, Brecksville, Ohio), and then the preservative and fragrance as called for. The pH of the resulting solution after the addition of hydrophobically-modified polymer, Potassium Acrylates Copolymer, (Ex. 968, Lubrizol, Brecksville, Ohio), was adjusted with a 20% solution of sodium hydroxide to a pH greater than 7.0. After the addition of preservative and fragrance, the pH of the resulting solution was adjusted with 20% solution of citric acid until the final desired pH was obtained. The remainder of the water was then added thereto. Formulas with the same components, but different pH were made from the same batch and samples were taken at different pH levels.

Example 10

Clarity Results for Inventive Examples E26-E31 at Different pH

The clarity of compositions of E26-E31 was determined according to the Clarity test and the Light Scattering test.

TABLE 10

| Ex | Surfactants | Surfactant (w/w %) | Anionic: Amphoteric | pH | Clarity (% T) | Count Rate (@7) kcts/s |
|---|---|---|---|---|---|---|
| E1 | Sodium Coco-Sulfate Sodium Lauryl Sulfoacetate Cocamidopropyl Hydroxysultaine | 13.6 | 0.3 | 6.0 | 90.2 | |
| E2 | Ammonium Lauryl Sulfate Cocamidopropyl Betaine | 6.2 | 0.4 | 6.0 | 98.5 | |
| E2 | Ammonium Lauryl Sulfate Cocamidopropyl Betaine | 6.2 | 0.4 | 4.8 | 77.9 | |
| E3 | Ammonium Lauryl Sulfate Cocamidopropyl Betaine | 3.1 | 0.4 | 6.0 | 99.1 | 15.7 |
| E3 | Ammonium Lauryl Sulfate Cocamidopropyl Betaine | 3.1 | 0.4 | 4.8 | 44.9 | 91.7 |
| E4 | Sodium Isotridecyl Alcohol Sulfate Cocamidopropyl Betaine | 7.2 | 0.6 | 4.8 | 99.3 | |
| E5 | Sodium Isotridecyl Alcohol Sulfate Disodium Lauryl Sulfosuccinate Cocamidopropyl Betaine | 7.2 | 1.5 | 4.8 | 98.7 | |

TABLE 10-continued

| Ex | Surfactants | Surfactant (w/w %) | Anionic: Amphoteric | pH | Clarity (% T) | Count Rate (@7) kcts/s |
|---|---|---|---|---|---|---|
| E6 | Alpha Olefin Sulfonate Cocamidopropyl Betaine | 3.5 | 4.0 | 5.5 | 95.4 | 32.7 |
| E6 | Alpha Olefin Sulfonate Cocamidopropyl Betaine | 3.5 | 4.0 | 4.8 | 94.8 | 36.7 |

The previous cleansing compositions, C1-C4 and C6-C10, shown, have contained amphoteric, nonionic and/or ethoxylated anionic surfactants. All of these cleansing compositions, at lower pH (i.e., below about 6.2), have demonstrated low clarity. All of the cleansing compositions in Table 8, C16, 18-25, contain the low Mw hydrophobically-modified polymer, Potassium Acrylates copolymer, and a range of non-ethoxylated anionic surfactants at levels above 2.0% actives, and all of these cleansing compositions have had high clarity.

Surprisingly, combining low MW hydrophobically-modified polymer, Potassium Acrylates copolymer, and non-ethoxylated anionic surfactants with amphoteric surfactants produces cleansing compositions that are clear below pH about 6.2 (E1-E6 from Table 10). In low MW hydrophobically-modified polymer, Potassium Acrylates copolymer, and non-ethoxylated anionic surfactant blends with amphoteric surfactant, the ratio of anionic:amphoteric surfactant is critical for achieving clarity at low pH. When the anionic:amphoteric surfactant ratio is less than about 0.5, clarity is achieved at pH less than about 6.2 but is not achieved at lower pH, i.e., less than about 4.8. The effect of anionic:amphoteric surfactant ratio on cleansing composition clarity is independent of total surfactant concentration. Surprisingly, in cleansing compositions with anionic:amphoteric surfactant ratio less than about 0.5, the concentration of non-ethoxylated anionic surfactant was less than about 2% actives and the cleansing compositions are clear at less than about 6.2 and greater than about 4.8.

When the anionic:amphoteric surfactant is greater than about 0.5, clarity is achieved at pH less than about 6.2. Clarity at low pH for anionic—amphoteric surfactant cleansing compositions with low MW hydrophobically-modified polymer, Potassium Acrylates copolymer, is achieved for non-ethoxylated anionic surfactants blended with amphoteric surfactants but is not achieved for low MW hydrophobically-modified polymer, Potassium Acrylates copolymer, and ethoxylated anionic surfactants blended with amphoteric surfactants.

| Example | absorbance | cocamidopropyl hydroxysultaine | cocamidopropyl betaine | Potassium Acrylates Copolymer | Water |
|---|---|---|---|---|---|
| Ea 32 | 0.05 | 1.3000 | 12.1000 | 0.21 | q.s. |
| Ea 33 | 0.08 | 0.6500 | 6.0500 | 1.11 | q.s. |
| Ea 34 | 0.15 | 0.3250 | 3.0250 | 1.55 | q.s. |
| Ea 35 | 0.15 | 0.1625 | 1.5125 | 1.78 | q.s. |
| Ea 36 | 0.14 | 0.0813 | 0.7563 | 1.89 | q.s. |
| Ea 37 | 0.13 | 0.0406 | 0.3781 | 1.94 | q.s. |

-continued

| Example | absorbance | cocamidopropyl hydroxysultaine | cocamidopropyl betaine | Potassium Acrylates Copolymer | Water |
|---|---|---|---|---|---|
| Ea 38 | 0.13 | 0.0203 | 0.1891 | 1.97 | q.s. |
| Ea 39 | 0.12 | 0.0102 | 0.0945 | 1.99 | q.s. |
| Ea 40 | 0.12 | 0.0051 | 0.0473 | 1.99 | q.s. |
| Ea 41 | 0.12 | 0.0025 | 0.0236 | 2.00 | q.s. |
| Ea 42 | 0.07 | 0.9750 | 9.0750 | 0.66 | q.s. |
| Ea 43 | 0.14 | 0.4875 | 4.5375 | 1.33 | q.s. |
| Ea 44 | 0.15 | 0.2438 | 2.2688 | 1.67 | q.s. |
| Ea 45 | 0.15 | 0.1219 | 1.1344 | 1.83 | q.s. |
| Ea 46 | 0.14 | 0.0609 | 0.5672 | 1.92 | q.s. |
| Ea 47 | 0.13 | 0.0305 | 0.2836 | 1.96 | q.s. |
| Ea 48 | 0.13 | 0.0152 | 0.1418 | 1.98 | q.s. |
| Ea 49 | 0.12 | 0.0076 | 0.0709 | 1.99 | q.s. |
| Ea 50 | 0.12 | 0.0038 | 0.0354 | 1.99 | q.s. |
| Ea 51 | 0.12 | 0.0019 | 0.0177 | 2.00 | q.s. |
| Ea 52 | 0.05 | 9.4000 | 4.0000 | 0.21 | q.s. |
| Ea 53 | 0.09 | 4.7000 | 2.0000 | 1.11 | q.s. |
| Ea 54 | 0.10 | 2.3500 | 1.0000 | 1.55 | q.s. |
| Ea 55 | 0.14 | 1.1750 | 0.5000 | 1.78 | q.s. |
| Ea 56 | 0.14 | 0.5875 | 0.2500 | 1.89 | q.s. |
| Ea 57 | 0.14 | 0.2938 | 0.1250 | 1.94 | q.s. |
| Ea 58 | 0.13 | 0.1469 | 0.0625 | 1.97 | q.s. |
| Ea 59 | 0.12 | 0.0734 | 0.0313 | 1.99 | q.s. |
| Ea 60 | 0.12 | 0.0367 | 0.0156 | 1.99 | q.s. |
| Ea 61 | 0.12 | 0.0184 | 0.0078 | 2.00 | q.s. |
| Ea 62 | 0.07 | 7.0500 | 3.0000 | 0.66 | q.s. |
| Ea 63 | 0.09 | 3.5250 | 1.5000 | 1.33 | q.s. |
| Ea 64 | 0.11 | 1.7625 | 0.7500 | 1.67 | q.s. |
| Ea 65 | 0.15 | 0.8813 | 0.3750 | 1.83 | q.s. |
| Ea 66 | 0.13 | 0.4406 | 0.1875 | 1.92 | q.s. |
| Ea 67 | 0.13 | 0.2203 | 0.0938 | 1.96 | q.s. |
| Ea 68 | 0.12 | 0.1102 | 0.0469 | 1.98 | q.s. |
| Ea 69 | 0.12 | 0.0551 | 0.0234 | 1.99 | q.s. |
| Ea 70 | 0.12 | 0.0275 | 0.0117 | 1.99 | q.s. |
| Ea 71 | 0.12 | 0.0138 | 0.0059 | 2.00 | q.s. |
| Ea 72 | 0.05 | 4.0000 | 9.4000 | 0.21 | q.s. |
| Ea 73 | 0.09 | 2.0000 | 4.7000 | 1.11 | q.s. |
| Ea 74 | 0.10 | 1.0000 | 2.3500 | 1.55 | q.s. |
| Ea 75 | 0.15 | 0.5000 | 1.1750 | 1.78 | q.s. |
| Ea 76 | 0.14 | 0.2500 | 0.5875 | 1.89 | q.s. |
| Ea 77 | 0.13 | 0.1250 | 0.2938 | 1.94 | q.s. |
| Ea 78 | 0.13 | 0.0625 | 0.1469 | 1.97 | q.s. |
| Ea 79 | 0.13 | 0.0313 | 0.0734 | 1.99 | q.s. |
| Ea 80 | 0.12 | 0.0156 | 0.0367 | 1.99 | q.s. |
| Ea 81 | 0.12 | 0.0078 | 0.0184 | 2.00 | q.s. |
| Ea 82 | 0.07 | 3.0000 | 7.0500 | 0.66 | q.s. |
| Ea 83 | 0.09 | 1.5000 | 3.5250 | 1.33 | q.s. |
| Ea 84 | 0.12 | 0.7500 | 1.7625 | 1.67 | q.s. |
| Ea 85 | 0.15 | 0.3750 | 0.8813 | 1.83 | q.s. |
| Ea 86 | 0.14 | 0.1875 | 0.4406 | 1.92 | q.s. |
| Ea 87 | 0.13 | 0.0938 | 0.2203 | 1.96 | q.s. |
| Ea 88 | 0.13 | 0.0469 | 0.1102 | 1.98 | q.s. |
| Ea 89 | 0.12 | 0.0234 | 0.0551 | 1.99 | q.s. |
| Ea 90 | 0.12 | 0.0117 | 0.0275 | 1.99 | q.s. |
| Ea 91 | 0.11 | 0.0059 | 0.0138 | 2.00 | q.s. |
| Ea 92 | 0.05 | 12.1000 | 1.3000 | 0.21 | q.s. |
| Ea 93 | 0.08 | 6.0500 | 0.6500 | 1.11 | q.s. |
| Ea 94 | 0.11 | 3.0250 | 0.3250 | 1.55 | q.s. |
| Ea 95 | 0.15 | 1.5125 | 0.1625 | 1.78 | q.s. |
| Ea 96 | 0.14 | 0.7563 | 0.0813 | 1.89 | q.s. |
| Ea 97 | 0.13 | 0.3781 | 0.0406 | 1.94 | q.s. |
| Ea 98 | 0.12 | 0.1891 | 0.0203 | 1.97 | q.s. |
| Ea 99 | 0.12 | 0.0945 | 0.0102 | 1.99 | q.s. |
| Ea 100 | 0.12 | 0.0473 | 0.0051 | 1.99 | q.s. |
| Ea 101 | 0.12 | 0.0236 | 0.0025 | 2.00 | q.s. |
| Ea 102 | 0.19 | 9.0750 | 0.9750 | 0.66 | q.s. |
| Ea 103 | 0.10 | 4.5375 | 0.4875 | 1.33 | q.s. |
| Ea 104 | 0.15 | 2.2688 | 0.2438 | 1.67 | q.s. |
| Ea 105 | 0.15 | 1.1344 | 0.1219 | 1.83 | q.s. |
| Ea 106 | 0.13 | 0.5672 | 0.0609 | 1.92 | q.s. |
| Ea 107 | 0.12 | 0.2836 | 0.0305 | 1.96 | q.s. |
| Ea 108 | 0.12 | 0.1418 | 0.0152 | 1.98 | q.s. |
| Ea 109 | 0.12 | 0.0709 | 0.0076 | 1.99 | q.s. |
| Ea 110 | 0.12 | 0.0354 | 0.0038 | 1.99 | q.s. |
| Ea 111 | 0.11 | 0.0177 | 0.0019 | 2.00 | q.s. |

Example 12

Examples Ea112-Ea190

Preparation of Cleansing Compositions

Cleansing compositions, Examples or Comparative examples 112-190, were prepared according to the materials and amounts listed in Table and under the Cleansing Mixing Procedure detailed above and at a pH of 5.5. The associated absorbance for each example as determined by the Absorbance Test is also shown.

| Example | absorbance | sodium lauroamp hoacetate | cocamidopropyl hydroxysultaine | Potassium Acrylates Copolymer | Water |
|---|---|---|---|---|---|
| Ea 112 | 0.06 | 1.3000 | 12.1000 | 0.21 | q.s. |
| Ea 113 | 0.12 | 0.6500 | 6.0500 | 1.11 | q.s. |
| Ea 114 | 0.11 | 0.3250 | 3.0250 | 1.55 | q.s. |
| Ea 115 | 0.16 | 0.1625 | 1.5125 | 1.78 | q.s. |
| Ea 116 | 0.15 | 0.0813 | 0.7563 | 1.89 | q.s. |
| Ea 117 | 0.15 | 0.0406 | 0.3781 | 1.94 | q.s. |
| Ea 118 | 0.14 | 0.0203 | 0.1891 | 1.97 | q.s. |
| Ea 119 | 0.14 | 0.0102 | 0.0945 | 1.99 | q.s. |
| Ea 120 | 0.13 | 0.0051 | 0.0473 | 1.99 | q.s. |
| Ea 121 | 0.16 | 0.0025 | 0.0236 | 2.00 | q.s. |
| Ea 122 | 0.07 | 0.9750 | 9.0750 | 0.66 | q.s. |
| Ea 123 | 0.11 | 0.4875 | 4.5375 | 1.33 | q.s. |
| Ea 124 | 0.13 | 0.2438 | 2.2688 | 1.67 | q.s. |
| Ea 125 | 0.16 | 0.1219 | 1.1344 | 1.83 | q.s. |
| Ea 126 | 0.15 | 0.0609 | 0.5672 | 1.92 | q.s. |
| Ea 127 | 0.14 | 0.0305 | 0.2836 | 1.96 | q.s. |
| Ea 128 | 0.13 | 0.0152 | 0.1418 | 1.98 | q.s. |
| Ea 129 | 0.14 | 0.0076 | 0.0709 | 1.99 | q.s. |
| Ea 130 | 0.13 | 0.0038 | 0.0354 | 1.99 | q.s. |
| Ea 131 | 0.14 | 0.0019 | 0.0177 | 2.00 | q.s. |
| Ea 132 | 0.06 | 9.4000 | 4.0000 | 0.21 | q.s. |
| Ea 133 | 0.11 | 4.7000 | 2.0000 | 1.11 | q.s. |
| Ea 134 | 0.12 | 2.3500 | 1.0000 | 1.55 | q.s. |
| Ea 135 | 0.16 | 1.1750 | 0.5000 | 1.78 | q.s. |
| Ea 136 | 0.16 | 0.5875 | 0.2500 | 1.89 | q.s. |
| Ea 137 | 0.15 | 0.2938 | 0.1250 | 1.94 | q.s. |
| Ea 138 | 0.14 | 0.1469 | 0.0625 | 1.97 | q.s. |
| Ea 139 | 0.13 | 0.0734 | 0.0313 | 1.99 | q.s. |
| Ea 140 | 0.13 | 0.0367 | 0.0156 | 1.99 | q.s. |
| Ea 141 | 0.14 | 0.0184 | 0.0078 | 2.00 | q.s. |
| Ea 142 | 0.11 | 7.0500 | 3.0000 | 0.66 | q.s. |
| Ea 143 | 0.11 | 3.5250 | 1.5000 | 1.33 | q.s. |
| Ea 144 | 0.14 | 1.7625 | 0.7500 | 1.67 | q.s. |
| Ea 145 | 0.15 | 0.8813 | 0.3750 | 1.83 | q.s. |
| Ea 146 | 0.15 | 0.4406 | 0.1875 | 1.92 | q.s. |
| Ea 147 | 0.15 | 0.2203 | 0.0938 | 1.96 | q.s. |
| Ea 148 | 0.14 | 0.1102 | 0.0469 | 1.98 | q.s. |
| Ea 149 | 0.14 | 0.0551 | 0.0234 | 1.99 | q.s. |
| Ea 150 | 0.13 | 0.0275 | 0.0117 | 1.99 | q.s. |
| Ea 151 | 0.14 | 0.0138 | 0.0059 | 2.00 | q.s. |
| Ea 152 | 0.06 | 4.0000 | 9.4000 | 0.21 | q.s. |
| Ea 153 | 0.09 | 2.0000 | 4.7000 | 1.11 | q.s. |
| Ea 154 | 0.11 | 1.0000 | 2.3500 | 1.55 | q.s. |
| Ea 155 | 0.15 | 0.5000 | 1.1750 | 1.78 | q.s. |
| Ea 156 | 0.15 | 0.2500 | 0.5875 | 1.89 | q.s. |
| Ea 157 | 0.15 | 0.1250 | 0.2938 | 1.94 | q.s. |
| Ea 158 | 0.14 | 0.0625 | 0.1469 | 1.97 | q.s. |
| Ea 159 | 0.14 | 0.0313 | 0.0734 | 1.99 | q.s. |
| Ea 160 | 0.14 | 0.0156 | 0.0367 | 1.99 | q.s. |
| Ea 161 | 0.13 | 0.0078 | 0.0184 | 2.00 | q.s. |
| Ea 162 | 0.07 | 3.0000 | 7.0500 | 0.66 | q.s. |
| Ea 163 | 0.11 | 1.5000 | 3.5250 | 1.33 | q.s. |
| Ea 164 | 0.14 | 0.7500 | 1.7625 | 1.67 | q.s. |
| Ea 165 | 0.16 | 0.3750 | 0.8813 | 1.83 | q.s. |
| Ea 166 | 0.15 | 0.1875 | 0.4406 | 1.92 | q.s. |
| Ea 167 | 0.14 | 0.0938 | 0.2203 | 1.96 | q.s. |
| Ea 168 | 0.14 | 0.0469 | 0.1102 | 1.98 | q.s. |
| Ea 169 | 0.13 | 0.0234 | 0.0551 | 1.99 | q.s. |
| Ea 170 | 0.14 | 0.0117 | 0.0275 | 1.99 | q.s. |
| Ea 171 | 0.13 | 0.0059 | 0.0138 | 2.00 | q.s. |
| Ea 172 | 0.13 | 6.0500 | 0.6500 | 1.11 | q.s. |
| Ea 173 | 0.13 | 3.0250 | 0.3250 | 1.55 | q.s. |
| Ea 174 | 0.17 | 1.5125 | 0.1625 | 1.78 | q.s. |
| Ea 175 | 0.16 | 0.7563 | 0.0813 | 1.89 | q.s. |
| Ea 176 | 0.15 | 0.3781 | 0.0406 | 1.94 | q.s. |
| Ea 177 | 0.14 | 0.1891 | 0.0203 | 1.97 | q.s. |
| Ea 178 | 0.14 | 0.0945 | 0.0102 | 1.99 | q.s. |
| Ea 179 | 0.14 | 0.0473 | 0.0051 | 1.99 | q.s. |
| Ea 180 | 0.13 | 0.0236 | 0.0025 | 2.00 | q.s. |
| Ea 181 | 0.10 | 9.0750 | 0.9750 | 0.66 | q.s. |
| Ea 182 | 0.15 | 4.5375 | 0.4875 | 1.33 | q.s. |
| Ea 183 | 0.16 | 2.2688 | 0.2438 | 1.67 | q.s. |
| Ea 184 | 0.17 | 1.1344 | 0.1219 | 1.83 | q.s. |
| Ea 185 | 0.16 | 0.5672 | 0.0609 | 1.92 | q.s. |
| Ea 186 | 0.15 | 0.2836 | 0.0305 | 1.96 | q.s. |
| Ea 187 | 0.14 | 0.1418 | 0.0152 | 1.98 | q.s. |
| Ea 188 | 0.14 | 0.0709 | 0.0076 | 1.99 | q.s. |
| Ea 189 | 0.14 | 0.0354 | 0.0038 | 1.99 | q.s. |
| Ea 190 | 0.13 | 0.0177 | 0.0019 | 2.00 | q.s. |

Example 13

Examples (Ea) and Comparative (Ca) 191-270

Preparation of Cleansing Compositions

The cleansing compositions, Examples or Comparatives 191-270, were prepared according to the materials and amounts listed in Table and under the Cleansing Mixing Procedure detailed above and at a pH of 5.5. The associated absorbance for each example as determined by the Absorbance Test is also shown.

| Example | absorbance | cocamidopropyl hydroxysultaine | coco betaine | Potassium Acrylates Copolymer | Water |
|---|---|---|---|---|---|
| Ea 191 | 0.06 | 1.3000 | 12.1000 | 0.54 | q.s. |
| Ca 192 | 1.45 | 0.6500 | 6.0500 | 2.77 | q.s. |
| Ca 193 | 1.83 | 0.3250 | 3.0250 | 3.88 | q.s. |
| Ca 194 | 2.04 | 0.1625 | 1.5125 | 4.44 | q.s. |
| Ca 195 | 1.18 | 0.0813 | 0.7563 | 4.72 | q.s. |
| Ca 196 | 1.90 | 0.0406 | 0.3781 | 4.86 | q.s. |
| Ca 197 | 1.89 | 0.0203 | 0.1891 | 4.93 | q.s. |
| Ca 198 | 1.89 | 0.0102 | 0.0945 | 4.97 | q.s. |
| Ca 199 | 1.88 | 0.0051 | 0.0473 | 4.98 | q.s. |
| Ca 200 | 1.87 | 0.0025 | 0.0236 | 4.99 | q.s. |
| Ca 201 | 0.44 | 0.9750 | 9.0750 | 1.65 | q.s. |
| Ca 202 | 0.62 | 0.4875 | 4.5375 | 3.33 | q.s. |
| Ca 203 | 2.09 | 0.2438 | 2.2688 | 4.16 | q.s. |
| Ca 204 | 0.14 | 0.1219 | 1.1344 | 4.58 | q.s. |
| Ca 205 | 1.80 | 0.0609 | 0.5672 | 4.79 | q.s. |
| Ca 206 | 1.87 | 0.0305 | 0.2836 | 4.90 | q.s. |
| Ca 207 | 1.87 | 0.0152 | 0.1418 | 4.95 | q.s. |
| Ca 208 | 1.86 | 0.0076 | 0.0709 | 4.97 | q.s. |
| Ca 209 | 1.86 | 0.0038 | 0.0354 | 4.99 | q.s. |
| Ca 210 | 1.86 | 0.0019 | 0.0177 | 4.99 | q.s. |
| Ea 211 | 0.07 | 9.4000 | 4.0000 | 0.54 | q.s. |
| Ca 212 | 1.12 | 4.7000 | 2.0000 | 2.77 | q.s. |
| Ca 213 | 1.60 | 2.3500 | 1.0000 | 3.88 | q.s. |
| Ca 214 | 1.87 | 1.1750 | 0.5000 | 4.44 | q.s. |
| Ca 215 | 1.85 | 0.5875 | 0.2500 | 4.72 | q.s. |
| Ca 216 | 1.87 | 0.2938 | 0.1250 | 4.86 | q.s. |
| Ca 217 | 1.87 | 0.1469 | 0.0625 | 4.93 | q.s. |
| Ca 218 | 1.87 | 0.0734 | 0.0313 | 4.97 | q.s. |
| Ca 219 | 1.87 | 0.0367 | 0.0156 | 4.98 | q.s. |
| Ca 220 | 1.85 | 0.0184 | 0.0078 | 4.99 | q.s. |
| Ca 221 | 0.17 | 7.0500 | 3.0000 | 1.65 | q.s. |
| Ca 222 | 1.30 | 3.5250 | 1.5000 | 3.33 | q.s. |

Example 14

Examples (Ea) and Comparative (Ca) 271-350

Preparation of Cleansing Compositions

The cleansing compositions, Examples or Comparatives 271-350, were prepared according to the materials and amounts listed in Table and under the Cleansing Mixing Procedure detailed above and at a pH of 5.5. The associated absorbance for each example as determined by the Absorbance Test is also shown.

| Example | absorbance | cocamidopropyl hydroxysultaine | coco betaine | Potassium Acrylates Copolymer | Water |
|---|---|---|---|---|---|
| Ca 223 | 1.74 | 1.7625 | 0.7500 | 4.16 | q.s. |
| Ca 224 | 1.87 | 0.8813 | 0.3750 | 4.58 | q.s. |
| Ca 225 | 1.85 | 0.4406 | 0.1875 | 4.79 | q.s. |
| Ca 226 | 1.87 | 0.2203 | 0.0938 | 4.90 | q.s. |
| Ca 227 | 1.87 | 0.1102 | 0.0469 | 4.95 | q.s. |
| Ca 228 | 1.87 | 0.0551 | 0.0234 | 4.97 | q.s. |
| Ca 229 | 1.87 | 0.0275 | 0.0117 | 4.99 | q.s. |
| Ca 230 | 1.86 | 0.0138 | 0.0059 | 4.99 | q.s. |
| Ea 231 | 0.06 | 4.0000 | 9.4000 | 0.54 | q.s. |
| Ca 232 | 1.33 | 2.0000 | 4.7000 | 2.77 | q.s. |
| Ca 233 | 1.67 | 1.0000 | 2.3500 | 3.88 | q.s. |
| Ca 234 | 1.80 | 0.5000 | 1.1750 | 4.44 | q.s. |
| Ca 235 | 1.85 | 0.2500 | 0.5875 | 4.72 | q.s. |
| Ca 236 | 1.89 | 0.1250 | 0.2938 | 4.86 | q.s. |
| Ca 237 | 1.90 | 0.0625 | 0.1469 | 4.93 | q.s. |
| Ca 238 | 1.88 | 0.0313 | 0.0734 | 4.97 | q.s. |
| Ca 239 | 1.88 | 0.0156 | 0.0367 | 4.98 | q.s. |
| Ca 240 | 1.86 | 0.0078 | 0.0184 | 4.99 | q.s. |
| Ca 241 | 0.98 | 3.0000 | 7.0500 | 1.65 | q.s. |
| Ca 242 | 1.20 | 1.5000 | 3.5250 | 3.33 | q.s. |
| Ca 243 | 1.79 | 0.7500 | 1.7625 | 4.16 | q.s. |
| Ca 244 | 1.83 | 0.3750 | 0.8813 | 4.58 | q.s. |
| Ca 245 | 1.86 | 0.1875 | 0.4406 | 4.79 | q.s. |
| Ca 246 | 1.87 | 0.0938 | 0.2203 | 4.90 | q.s. |
| Ca 247 | 1.91 | 0.0469 | 0.1102 | 4.95 | q.s. |
| Ca 248 | 1.88 | 0.0234 | 0.0551 | 4.97 | q.s. |
| Ca 249 | 1.88 | 0.0117 | 0.0275 | 4.99 | q.s. |
| Ca 250 | 1.87 | 0.0059 | 0.0138 | 4.99 | q.s. |
| Ca 251 | 0.07 | 12.1000 | 1.3000 | 0.54 | q.s. |
| Ca 252 | 1.31 | 6.0500 | 0.6500 | 2.77 | q.s. |
| Ca 253 | 1.77 | 3.0250 | 0.3250 | 3.88 | q.s. |
| Ca 254 | 1.83 | 1.5125 | 0.1625 | 4.44 | q.s. |
| Ca 255 | 1.87 | 0.7563 | 0.0813 | 4.72 | q.s. |
| Ca 256 | 1.86 | 0.3781 | 0.0406 | 4.86 | q.s. |
| Ca 257 | 1.88 | 0.1891 | 0.0203 | 4.93 | q.s. |
| Ca 258 | 1.87 | 0.0945 | 0.0102 | 4.97 | q.s. |
| Ca 259 | 1.87 | 0.0473 | 0.0051 | 4.98 | q.s. |
| Ca 260 | 1.87 | 0.0236 | 0.0025 | 4.99 | q.s. |
| Ca 261 | 0.33 | 9.0750 | 0.9750 | 1.65 | q.s. |
| Ca 262 | 1.44 | 4.5375 | 0.4875 | 3.33 | q.s. |
| Ca 263 | 1.79 | 2.2688 | 0.2438 | 4.16 | q.s. |
| Ca 264 | 1.86 | 1.1344 | 0.1219 | 4.58 | q.s. |
| Ca 265 | 1.88 | 0.5672 | 0.0609 | 4.79 | q.s. |
| Ca 266 | 1.89 | 0.2836 | 0.0305 | 4.90 | q.s. |
| Ca 267 | 1.90 | 0.1418 | 0.0152 | 4.95 | q.s. |
| Ca 268 | 1.90 | 0.0709 | 0.0076 | 4.97 | q.s. |
| Ca 269 | 1.90 | 0.0354 | 0.0038 | 4.99 | q.s. |
| Ca 270 | 1.89 | 0.0177 | 0.0019 | 4.99 | q.s. |
| Ea 271 | 0.07 | 1.3000 | 12.1000 | 1.07 | q.s. |
| Ca 272 | 1.43 | 0.6500 | 6.0500 | 5.54 | q.s. |
| Ca 273 | 2.28 | 0.3250 | 3.0250 | 7.77 | q.s. |
| Ca 274 | 2.06 | 0.1625 | 1.5125 | 8.88 | q.s. |
| Ca 275 | 2.04 | 0.0813 | 0.7563 | 9.44 | q.s. |
| Ca 276 | 2.04 | 0.0406 | 0.3781 | 9.72 | q.s. |
| Ca 277 | 1.89 | 0.0203 | 0.1891 | 9.86 | q.s. |
| Ca 278 | 1.96 | 0.0102 | 0.0945 | 9.93 | q.s. |
| Ca 279 | 2.14 | 0.0051 | 0.0473 | 9.97 | q.s. |
| Ca 280 | 1.71 | 0.0025 | 0.0236 | 9.98 | q.s. |
| Ca 281 | 0.21 | 0.9750 | 9.0750 | 3.30 | q.s. |
| Ca 282 | 1.80 | 0.4875 | 4.5375 | 6.65 | q.s. |
| Ca 283 | 1.96 | 0.2438 | 2.2688 | 8.33 | q.s. |
| Ca 284 | 2.00 | 0.1219 | 1.1344 | 9.16 | q.s. |
| Ca 285 | 2.01 | 0.0609 | 0.5672 | 9.58 | q.s. |
| Ca 286 | 2.01 | 0.0305 | 0.2836 | 9.79 | q.s. |
| Ca 287 | 2.03 | 0.0152 | 0.1418 | 9.90 | q.s. |
| Ca 288 | 1.97 | 0.0076 | 0.0709 | 9.95 | q.s. |
| Ca 289 | 2.03 | 0.0038 | 0.0354 | 9.97 | q.s. |
| Ca 290 | 2.00 | 0.0019 | 0.0177 | 9.99 | q.s. |
| Ea 291 | 0.07 | 9.4000 | 4.0000 | 1.07 | q.s. |
| Ca 292 | 1.67 | 4.7000 | 2.0000 | 5.54 | q.s. |
| Ca 293 | 1.94 | 2.3500 | 1.0000 | 7.77 | q.s. |
| Ca 294 | 1.98 | 1.1750 | 0.5000 | 8.88 | q.s. |
| Ca 295 | 2.00 | 0.5875 | 0.2500 | 9.44 | q.s. |
| Ca 296 | 2.00 | 0.2938 | 0.1250 | 9.72 | q.s. |
| Ca 297 | 2.01 | 0.1469 | 0.0625 | 9.86 | q.s. |
| Ca 298 | 2.01 | 0.0734 | 0.0313 | 9.93 | q.s. |
| Ca 299 | 2.01 | 0.0367 | 0.0156 | 9.97 | q.s. |
| Ca 300 | 1.99 | 0.0184 | 0.0078 | 9.98 | q.s. |
| Ca 301 | 0.82 | 7.0500 | 3.0000 | 3.30 | q.s. |
| Ca 302 | 1.74 | 3.5250 | 1.5000 | 6.65 | q.s. |
| Ca 303 | 1.96 | 1.7625 | 0.7500 | 8.33 | q.s. |
| Ca 304 | 1.99 | 0.8813 | 0.3750 | 9.16 | q.s. |
| Ca 305 | 2.00 | 0.4406 | 0.1875 | 9.58 | q.s. |
| Ca 306 | 2.01 | 0.2203 | 0.0938 | 9.79 | q.s. |
| Ca 307 | 2.01 | 0.1102 | 0.0469 | 9.90 | q.s. |
| Ca 308 | 2.01 | 0.0551 | 0.0234 | 9.95 | q.s. |
| Ca 309 | 1.99 | 0.0275 | 0.0117 | 9.97 | q.s. |
| Ca 310 | 1.99 | 0.0138 | 0.0059 | 9.99 | q.s. |
| Ea 311 | 0.09 | 4.0000 | 9.4000 | 1.07 | q.s. |
| Ca 312 | 1.66 | 2.0000 | 4.7000 | 5.54 | q.s. |
| Ca 313 | 1.92 | 1.0000 | 2.3500 | 7.77 | q.s. |
| Ca 314 | 1.96 | 0.5000 | 1.1750 | 8.88 | q.s. |
| Ca 315 | 2.01 | 0.2500 | 0.5875 | 9.44 | q.s. |
| Ca 316 | 2.00 | 0.1250 | 0.2938 | 9.72 | q.s. |
| Ca 317 | 2.02 | 0.0625 | 0.1469 | 9.86 | q.s. |
| Ca 318 | 2.01 | 0.0313 | 0.0734 | 9.93 | q.s. |
| Ca 319 | 2.02 | 0.0156 | 0.0367 | 9.97 | q.s. |
| Ca 320 | 1.99 | 0.0078 | 0.0184 | 9.98 | q.s. |
| Ca 321 | 1.12 | 3.0000 | 7.0500 | 3.30 | q.s. |
| Ca 322 | 1.76 | 1.5000 | 3.5250 | 6.65 | q.s. |
| Ca 323 | 1.94 | 0.7500 | 1.7625 | 8.33 | q.s. |
| Ca 324 | 2.00 | 0.3750 | 0.8813 | 9.16 | q.s. |
| Ca 325 | 1.99 | 0.1875 | 0.4406 | 9.58 | q.s. |
| Ca 326 | 2.01 | 0.0938 | 0.2203 | 9.79 | q.s. |
| Ca 327 | 2.02 | 0.0469 | 0.1102 | 9.90 | q.s. |
| Ca 328 | 2.01 | 0.0234 | 0.0551 | 9.95 | q.s. |
| Ca 329 | 2.01 | 0.0117 | 0.0275 | 9.97 | q.s. |
| Ca 330 | 2.00 | 0.0059 | 0.0138 | 9.99 | q.s. |
| Ca 331 | 0.12 | 12.1000 | 1.3000 | 1.07 | q.s. |
| Ca 332 | 1.82 | 6.0500 | 0.6500 | 5.54 | q.s. |
| Ca 333 | 1.96 | 3.0250 | 0.3250 | 7.77 | q.s. |
| Ca 334 | 1.99 | 1.5125 | 0.1625 | 8.88 | q.s. |
| Ca 335 | 2.00 | 0.7563 | 0.0813 | 9.44 | q.s. |
| Ca 336 | 2.01 | 0.3781 | 0.0406 | 9.72 | q.s. |
| Ca 337 | 2.02 | 0.1891 | 0.0203 | 9.86 | q.s. |
| Ca 338 | 2.01 | 0.0945 | 0.0102 | 9.93 | q.s. |
| Ca 339 | 2.01 | 0.0473 | 0.0051 | 9.97 | q.s. |
| Ca 340 | 2.01 | 0.0236 | 0.0025 | 9.98 | q.s. |
| Ca 341 | 1.37 | 9.0750 | 0.9750 | 3.30 | q.s. |
| Ca 342 | 1.89 | 4.5375 | 0.4875 | 6.65 | q.s. |
| Ca 343 | 1.99 | 2.2688 | 0.2438 | 8.33 | q.s. |
| Ca 344 | 2.02 | 1.1344 | 0.1219 | 9.16 | q.s. |
| Ca 345 | 2.04 | 0.5672 | 0.0609 | 9.58 | q.s. |
| Ca 346 | 2.04 | 0.2836 | 0.0305 | 9.79 | q.s. |
| Ca 347 | 2.05 | 0.1418 | 0.0152 | 9.90 | q.s. |
| Ca 348 | 2.04 | 0.0709 | 0.0076 | 9.95 | q.s. |

| Example | absorbance | cocamidopropyl hydroxysultaine | coco betaine | Potassium Acrylates Copolymer | Water |
|---|---|---|---|---|---|
| Ca 349 | 2.04 | 0.0354 | 0.0038 | 9.97 | q.s. |
| Ca 350 | 2.03 | 0.0177 | 0.0019 | 9.99 | q.s. |

Example 15

Examples (Ea) and Comparative (Ca) 351-430

Preparation of Cleansing Compositions

The cleansing compositions, Examples or Comparatives 351-430, were prepared according to the materials and amounts listed in Table and under the Cleansing Mixing Procedure detailed above and at a pH of 5.5. The associated absorbance for each example as determined by the Absorbance Test is also shown.

| Example | absorbance | cocamidopropyl hydroxysultaine | coco betaine | Potassium Acrylates Copolymer | Water |
|---|---|---|---|---|---|
| Ea 351 | 0.05 | 1.3000 | 12.1000 | 0.21 | q.s. |
| Ea 352 | 0.10 | 0.6500 | 6.0500 | 1.11 | q.s. |
| Ca 353 | 0.56 | 0.3250 | 3.0250 | 1.55 | q.s. |
| Ca 354 | 0.93 | 0.1625 | 1.5125 | 1.78 | q.s. |
| Ca 355 | 0.46 | 0.0813 | 0.7563 | 1.89 | q.s. |
| Ca 356 | 0.53 | 0.0406 | 0.3781 | 1.94 | q.s. |
| Ca 357 | 0.37 | 0.0203 | 0.1891 | 1.97 | q.s. |
| Ca 358 | 0.25 | 0.0102 | 0.0945 | 1.99 | q.s. |
| Ca 359 | 0.19 | 0.0051 | 0.0473 | 1.99 | q.s. |
| Ca 360 | 0.16 | 0.0025 | 0.0236 | 2.00 | q.s. |
| Ea 361 | 0.08 | 0.9750 | 9.0750 | 0.66 | q.s. |
| Ea 362 | 0.15 | 0.4875 | 4.5375 | 1.33 | q.s. |
| Ca 363 | 0.83 | 0.2438 | 2.2688 | 1.67 | q.s. |
| Ca 364 | 0.52 | 0.1219 | 1.1344 | 1.83 | q.s. |
| Ca 365 | 0.43 | 0.0609 | 0.5672 | 1.92 | q.s. |
| Ca 366 | 0.37 | 0.0305 | 0.2836 | 1.96 | q.s. |
| Ca 367 | 0.27 | 0.0152 | 0.1418 | 1.98 | q.s. |
| Ca 368 | 0.20 | 0.0076 | 0.0709 | 1.99 | q.s. |
| Ca 369 | 0.17 | 0.0038 | 0.0354 | 1.99 | q.s. |
| Ca 370 | 0.14 | 0.0019 | 0.0177 | 2.00 | q.s. |
| Ea 371 | 0.05 | 9.4000 | 4.0000 | 0.21 | q.s. |
| Ca 372 | 0.12 | 4.7000 | 2.0000 | 1.11 | q.s. |
| Ca 373 | 0.18 | 2.3500 | 1.0000 | 1.55 | q.s. |
| Ca 374 | 0.19 | 1.1750 | 0.5000 | 1.78 | q.s. |
| Ca 375 | 0.16 | 0.5875 | 0.2500 | 1.89 | q.s. |
| Ca 376 | 0.15 | 0.2938 | 0.1250 | 1.94 | q.s. |
| Ca 377 | 0.15 | 0.1469 | 0.0625 | 1.97 | q.s. |
| Ca 378 | 0.14 | 0.0734 | 0.0313 | 1.99 | q.s. |
| Ca 379 | 0.14 | 0.0367 | 0.0156 | 1.99 | q.s. |
| Ca 380 | 0.14 | 0.0184 | 0.0078 | 2.00 | q.s. |
| Ca 381 | 0.08 | 7.0500 | 3.0000 | 0.66 | q.s. |
| Ca 382 | 0.18 | 3.5250 | 1.5000 | 1.33 | q.s. |
| Ca 383 | 0.24 | 1.7625 | 0.7500 | 1.67 | q.s. |
| Ca 384 | 0.19 | 0.8813 | 0.3750 | 1.83 | q.s. |
| Ca 385 | 0.18 | 0.4406 | 0.1875 | 1.92 | q.s. |
| Ca 386 | 0.16 | 0.2203 | 0.0938 | 1.96 | q.s. |
| Ca 387 | 0.15 | 0.1102 | 0.0469 | 1.98 | q.s. |
| Ca 388 | 0.14 | 0.0551 | 0.0234 | 1.99 | q.s. |
| Ca 389 | 0.14 | 0.0275 | 0.0117 | 1.99 | q.s. |
| Ca 390 | 0.14 | 0.0138 | 0.0059 | 2.00 | q.s. |
| Ea 391 | 0.06 | 4.0000 | 9.4000 | 0.21 | q.s. |
| Ea 392 | 0.12 | 2.0000 | 4.7000 | 1.11 | q.s. |
| Ca 393 | 0.56 | 1.0000 | 2.3500 | 1.55 | q.s. |
| Ca 394 | 0.57 | 0.5000 | 1.1750 | 1.78 | q.s. |
| Ca 395 | 0.36 | 0.2500 | 0.5875 | 1.89 | q.s. |
| Ca 396 | 0.35 | 0.1250 | 0.2938 | 1.94 | q.s. |
| Ca 397 | 0.24 | 0.0625 | 0.1469 | 1.97 | q.s. |
| Ca 398 | 0.19 | 0.0313 | 0.0734 | 1.99 | q.s. |
| Ca 399 | 0.16 | 0.0156 | 0.0367 | 1.99 | q.s. |
| Ca 400 | 0.15 | 0.0078 | 0.0184 | 2.00 | q.s. |
| Ea 401 | 0.07 | 3.0000 | 7.0500 | 0.66 | q.s. |
| Ea 402 | 0.19 | 1.5000 | 3.5250 | 1.33 | q.s. |
| Ca 403 | 0.58 | 0.7500 | 1.7625 | 1.67 | q.s. |
| Ca 404 | 0.62 | 0.3750 | 0.8813 | 1.83 | q.s. |
| Ca 405 | 0.34 | 0.1875 | 0.4406 | 1.92 | q.s. |
| Ca 406 | 0.32 | 0.0938 | 0.2203 | 1.96 | q.s. |
| Ca 407 | 0.25 | 0.0469 | 0.1102 | 1.98 | q.s. |
| Ca 408 | 0.19 | 0.0234 | 0.0551 | 1.99 | q.s. |
| Ca 409 | 0.16 | 0.0117 | 0.0275 | 1.99 | q.s. |
| Ca 410 | 0.15 | 0.0059 | 0.0138 | 2.00 | q.s. |
| Ca 411 | 0.06 | 12.1000 | 1.3000 | 0.21 | q.s. |
| Ca 412 | 0.10 | 6.0500 | 0.6500 | 1.11 | q.s. |
| Ca 413 | 0.16 | 3.0250 | 0.3250 | 1.55 | q.s. |
| Ca 414 | 0.18 | 1.5125 | 0.1625 | 1.78 | q.s. |
| Ca 415 | 0.16 | 0.7563 | 0.0813 | 1.89 | q.s. |
| Ca 416 | 0.15 | 0.3781 | 0.0406 | 1.94 | q.s. |
| Ca 417 | 0.14 | 0.1891 | 0.0203 | 1.97 | q.s. |
| Ca 418 | 0.14 | 0.0945 | 0.0102 | 1.99 | q.s. |
| Ca 419 | 0.14 | 0.0473 | 0.0051 | 1.99 | q.s. |
| Ca 420 | 0.14 | 0.0236 | 0.0025 | 2.00 | q.s. |
| Ca 421 | 0.08 | 9.0750 | 0.9750 | 0.66 | q.s. |
| Ca 422 | 0.11 | 4.5375 | 0.4875 | 1.33 | q.s. |
| Ca 423 | 0.17 | 2.2688 | 0.2438 | 1.67 | q.s. |
| Ca 424 | 0.17 | 1.1344 | 0.1219 | 1.83 | q.s. |
| Ca 425 | 0.15 | 0.5672 | 0.0609 | 1.92 | q.s. |
| Ca 426 | 0.15 | 0.2836 | 0.0305 | 1.96 | q.s. |
| Ca 427 | 0.14 | 0.1418 | 0.0152 | 1.98 | q.s. |
| Ca 428 | 0.14 | 0.0709 | 0.0076 | 1.99 | q.s. |
| Ca 429 | 0.14 | 0.0354 | 0.0038 | 1.99 | q.s. |
| Ca 430 | 0.14 | 0.0177 | 0.0019 | 2.00 | q.s. |

Example 16

Examples (Ea) and Comparative (Ca) 431-510

Preparation of Cleansing Compositions

The cleansing compositions, Examples or Comparatives 431-510, were prepared according to the materials and amounts listed in Table and under the Cleansing Mixing Procedure detailed above and all at a pH of 5.5. The associated absorbance for each example as determined by the Absorbance Test is also shown.

| Example | absorbance | sodium lauroamphoacetate | coco betaine | Potassium Acrylates Copolymer | Water |
|---|---|---|---|---|---|
| Ea 431 | 0.05 | 1.3000 | 12.1000 | 0.21 | q.s. |
| Ea 432 | 0.11 | 0.6500 | 6.0500 | 1.11 | q.s. |
| Ca 433 | 0.53 | 0.3250 | 3.0250 | 1.55 | q.s. |
| Ca 434 | 0.84 | 0.1625 | 1.5125 | 1.78 | q.s. |
| Ca 435 | 0.50 | 0.0813 | 0.7563 | 1.89 | q.s. |
| Ca 436 | 0.63 | 0.0406 | 0.3781 | 1.94 | q.s. |
| Ca 437 | 0.41 | 0.0203 | 0.1891 | 1.97 | q.s. |
| Ca 438 | 0.28 | 0.0102 | 0.0945 | 1.99 | q.s. |
| Ca 439 | 0.20 | 0.0051 | 0.0473 | 1.99 | q.s. |
| Ca 440 | 0.17 | 0.0025 | 0.0236 | 2.00 | q.s. |
| Ea 441 | 0.08 | 0.9750 | 9.0750 | 0.66 | q.s. |
| Ea 442 | 0.15 | 0.4875 | 4.5375 | 1.33 | q.s. |
| Ca 443 | 0.60 | 0.2438 | 2.2688 | 1.67 | q.s. |
| Ca 444 | 0.65 | 0.1219 | 1.1344 | 1.83 | q.s. |
| Ca 445 | 0.64 | 0.0609 | 0.5672 | 1.92 | q.s. |
| Ca 446 | 0.53 | 0.0305 | 0.2836 | 1.96 | q.s. |
| Ca 447 | 0.36 | 0.0152 | 0.1418 | 1.98 | q.s. |
| Ca 448 | 0.24 | 0.0076 | 0.0709 | 1.99 | q.s. |

-continued

| Example | absorbance | sodium lauroamphoacetate | coco betaine | Potassium Acrylates Copolymer | Water |
|---|---|---|---|---|---|
| Ca 449 | 0.19 | 0.0038 | 0.0354 | 1.99 | q.s. |
| Ca 450 | 0.17 | 0.0019 | 0.0177 | 2.00 | q.s. |
| Ea 451 | 0.07 | 9.4000 | 4.0000 | 0.21 | q.s. |
| Ca 452 | 0.14 | 4.7000 | 2.0000 | 1.11 | q.s. |
| Ca 453 | 0.18 | 2.3500 | 1.0000 | 1.55 | q.s. |
| Ca 454 | 0.20 | 1.1750 | 0.5000 | 1.78 | q.s. |
| Ca 455 | 0.18 | 0.5875 | 0.2500 | 1.89 | q.s. |
| Ca 456 | 0.17 | 0.2938 | 0.1250 | 1.94 | q.s. |
| Ca 457 | 0.16 | 0.1469 | 0.0625 | 1.97 | q.s. |
| Ca 458 | 0.15 | 0.0734 | 0.0313 | 1.99 | q.s. |
| Ca 459 | 0.14 | 0.0367 | 0.0156 | 1.99 | q.s. |
| Ca 460 | 0.14 | 0.0184 | 0.0078 | 2.00 | q.s. |
| Ca 461 | 0.09 | 7.0500 | 3.0000 | 0.66 | q.s. |
| Ca 462 | 0.35 | 3.5250 | 1.5000 | 1.33 | q.s. |
| Ca 463 | 0.20 | 1.7625 | 0.7500 | 1.67 | q.s. |
| Ca 464 | 0.19 | 0.8813 | 0.3750 | 1.83 | q.s. |
| Ca 465 | 0.18 | 0.4406 | 0.1875 | 1.92 | q.s. |
| Ca 466 | 0.16 | 0.2203 | 0.0938 | 1.96 | q.s. |
| Ca 467 | 0.16 | 0.1102 | 0.0469 | 1.98 | q.s. |
| Ca 468 | 0.16 | 0.0551 | 0.0234 | 1.99 | q.s. |
| Ca 469 | 0.14 | 0.0275 | 0.0117 | 1.99 | q.s. |
| Ca 470 | 0.14 | 0.0138 | 0.0059 | 2.00 | q.s. |
| Ea 471 | 0.05 | 4.0000 | 9.4000 | 0.21 | q.s. |
| Ea 472 | 0.12 | 2.0000 | 4.7000 | 1.11 | q.s. |
| Ca 473 | 0.44 | 1.0000 | 2.3500 | 1.55 | q.s. |
| Ca 474 | 0.55 | 0.5000 | 1.1750 | 1.78 | q.s. |
| Ca 475 | 0.41 | 0.2500 | 0.5875 | 1.89 | q.s. |
| Ca 476 | 0.43 | 0.1250 | 0.2938 | 1.94 | q.s. |
| Ca 477 | 0.33 | 0.0625 | 0.1469 | 1.97 | q.s. |
| Ca 478 | 0.24 | 0.0313 | 0.0734 | 1.99 | q.s. |
| Ca 479 | 0.19 | 0.0156 | 0.0367 | 1.99 | q.s. |
| Ca 480 | 0.16 | 0.0078 | 0.0184 | 2.00 | q.s. |
| Ea 481 | 0.08 | 3.0000 | 7.0500 | 0.66 | q.s. |
| Ea 482 | 0.18 | 1.5000 | 3.5250 | 1.33 | q.s. |
| Ca 483 | 0.47 | 0.7500 | 1.7625 | 1.67 | q.s. |
| Ca 484 | 0.47 | 0.3750 | 0.8813 | 1.83 | q.s. |
| Ca 485 | 0.43 | 0.1875 | 0.4406 | 1.92 | q.s. |
| Ca 486 | 0.39 | 0.0938 | 0.2203 | 1.96 | q.s. |
| Ca 487 | 0.27 | 0.0469 | 0.1102 | 1.98 | q.s. |
| Ca 488 | 0.21 | 0.0234 | 0.0551 | 1.99 | q.s. |
| Ca 489 | 0.17 | 0.0117 | 0.0275 | 1.99 | q.s. |
| Ca 490 | 0.15 | 0.0059 | 0.0138 | 2.00 | q.s. |
| Ca 491 | 0.06 | 12.1000 | 1.3000 | 0.21 | q.s. |
| Ca 492 | 0.17 | 6.0500 | 0.6500 | 1.11 | q.s. |
| Ca 493 | 0.18 | 3.0250 | 0.3250 | 1.55 | q.s. |
| Ca 494 | 0.17 | 1.5125 | 0.1625 | 1.78 | q.s. |
| Ca 495 | 0.16 | 0.7563 | 0.0813 | 1.89 | q.s. |
| Ca 496 | 0.15 | 0.3781 | 0.0406 | 1.94 | q.s. |
| Ca 497 | 0.15 | 0.1891 | 0.0203 | 1.97 | q.s. |
| Ca 498 | 0.14 | 0.0945 | 0.0102 | 1.99 | q.s. |
| Ca 499 | 0.14 | 0.0473 | 0.0051 | 1.99 | q.s. |
| Ca 500 | 0.13 | 0.0236 | 0.0025 | 2.00 | q.s. |
| Ca 501 | 0.10 | 9.0750 | 0.9750 | 0.66 | q.s. |
| Ca 502 | 0.16 | 4.5375 | 0.4875 | 1.33 | q.s. |
| Ca 503 | 0.19 | 2.2688 | 0.2438 | 1.67 | q.s. |
| Ca 504 | 0.17 | 1.1344 | 0.1219 | 1.83 | q.s. |
| Ca 505 | 0.15 | 0.5672 | 0.0609 | 1.92 | q.s. |
| Ca 506 | 0.15 | 0.2836 | 0.0305 | 1.96 | q.s. |
| Ca 507 | 0.14 | 0.1418 | 0.0152 | 1.98 | q.s. |
| Ca 508 | 0.14 | 0.0709 | 0.0076 | 1.99 | q.s. |
| Ca 509 | 0.14 | 0.0354 | 0.0038 | 1.99 | q.s. |
| Ca 510 | 0.13 | 0.0177 | 0.0019 | 2.00 | q.s. |

While it is often desirable to achieve a clear cleansing formula, it is nearly always necessary for cleansing formulas to be stable, i.e. not macroscopically phase separated.

Certain combinations of surfactants and anionic polymers can lead to very hazy or even unstable solutions.

In aqueous solutions, polymers with hydrophobic character can interact with surfactants and form larger complexes, which are a form of microscopic phase separation. Sufficiently large, these larger complexes will scatter light and create hazy, or unclear, formulas. As these complexes get larger and larger the cleanser will become less clear and possible exhibit macroscopic phase separation.

The above examples show the resultant clarity from a series of different cleanser formulas that cover a range of: amphoteric surfactant types (CAPB, SLAC, CB, COHS), surfactant concentrations, and hydrophobically-modified polymer concentrations. We surprisingly find that clear or fairly clear and stable cleansing formulas can be made at low pH, but with only certain combinations. High hydrophobically-modified polymer concentrations are found to lead to hazy or unstable cleansing formulas.

What is claimed is:

1. A clear skin cleansing composition comprising:
   (a) water;
   (b) a low molecular weight non-crosslinked, linear acrylic copolymer in an amount comprising from about 0.03 weight percent to about 2.1 weight percent of the skin cleansing composition;
   (c) a surfactant component comprising a surfactant selected from the group consisting of, a blend of at least two amphoteric surfactants selected from the group consisting of: an ampholytic synthetic surfactant comprising a derivative of an aliphatic amine having from 8 to 18 carbon atoms and an anionic water-solubilizing group and zwitterionic surfactants comprising internally neutralized derivatives of aliphatic quaternary ammonium, phosphonium and tertiary sulfonium compounds, in which the aliphatic radical is straight chain or branched and wherein one of the aliphatic substituents has from 8 to 18 carbon atoms and one contains an anionic water-solubilizing group wherein said skin cleansing composition has a pH of less than about 6 and is substantially free of anionic surfactant and cocobetaine, said surfactants being present in a concentration of between about 0.0015 to about 15 weight percent of the skin cleansing composition and the total surfactant load of such composition is less than about 20 weight percent; said skin cleansing composition having an absorbance of less than about 0.22 as determined by the Clarity Absorbance Test.

2. A clear skin cleansing composition according to claim 1 wherein said surfactant component is selected from the group consisting of sodium lauroamphoacetate, cocamidopropyl betaine and cocamidopropyl hydroxysultaine.

3. A clear skin cleansing composition comprising:
   (a) water;
   (b) a low molecular weight non-crosslinked, linear acrylic copolymer in an amount comprising from about 0.03 weight percent to about 1.6 weight percent of the skin cleansing composition;
   (c) at least two amphoteric surfactants selected from the group consisting of: an ampholytic synthetic surfactant comprising a derivative of an aliphatic amine having from 8 to 18 carbon atoms and an anionic water-solubilizing group and zwitterionic surfactants comprising internally neutralized derivatives of aliphatic quaternary ammonium, phosphonium and tertiary sulfonium compounds, in which the aliphatic radical is straight chain or branched and wherein one of the aliphatic substituents has from 8 to 18 carbon atoms and one contains an anionic water-solubilizing group; one of such amphoteric surfactants comprising coco-betaine in a concentration of less than about 0.065 weight percent or greater than about 3.5 weight percent; said remaining amphoteric surfactants being present in a concentration of between about 0.0015 to about 15 weight percent of the skin cleansing composition and the total surfactant load of such composition is less than about 20 weight percent;

wherein said skin cleansing composition has a pH of less than about 6 and is substantially free of anionic surfactant, said skin cleansing composition having an absorbance of less than about 0.22 as determined by the Clarity Absorbance Test.

4. A clear skin cleansing composition according to claim 3 wherein said surfactant component further comprises an amphoteric surfactant selected from the group consisting of sodium lauroamphoacetate, cocamidopropyl betaine and cocamidopropyl hydroxysultaine.

* * * * *